(12) United States Patent
Nakajima et al.

(10) Patent No.: US 7,968,837 B2
(45) Date of Patent: Jun. 28, 2011

(54) SEPARATE-TYPE DETECTOR WITH REDUNDANT SYNCHRONIZATION FEATURE

(75) Inventors: Satoshi Nakajima, Tokyo (JP); Masayuki Itou, Tokyo (JP)

(73) Assignee: Hochiki Corporation, Tokyo (JP)

( * ) Notice: Subject to any disclaimer, the term of this patent is extended or adjusted under 35 U.S.C. 154(b) by 79 days.

(21) Appl. No.: 12/280,536

(22) PCT Filed: Feb. 23, 2006

(86) PCT No.: PCT/JP2006/303260
§ 371 (c)(1),
(2), (4) Date: Oct. 2, 2008

(87) PCT Pub. No.: WO2007/096964
PCT Pub. Date: Aug. 30, 2007

(65) Prior Publication Data
US 2009/0026354 A1    Jan. 29, 2009

(51) Int. Cl.
*G06M 7/00*    (2006.01)
(52) U.S. Cl. ......... 250/221; 340/555; 340/556; 340/557
(58) Field of Classification Search .................. 250/221; 340/555, 556, 557
See application file for complete search history.

(56) References Cited

U.S. PATENT DOCUMENTS

| | | | |
|---|---|---|---|
| 3,098,932 A | 7/1963 | Laudon | |
| 5,130,532 A * | 7/1992 | Clemens | ........................ 250/221 |
| 2004/0155790 A1 | 8/2004 | Tsuji | |

FOREIGN PATENT DOCUMENTS

| | | | |
|---|---|---|---|
| JP | 5-225465 A | 9/1993 | |
| JP | 8-227489 A | 9/1996 | |
| JP | 11-053657 A | 2/1999 | |
| JP | 2000-113338 A | 4/2000 | |
| JP | 2000182176 A | 6/2000 | |
| JP | 2001235367 A | 8/2001 | |
| JP | 2001356047 A | 12/2001 | |
| JP | 2004229069 A | 8/2004 | |
| JP | 2005-63265 A | 3/2005 | |
| JP | 2005-063265 A | 3/2005 | |

OTHER PUBLICATIONS

PCT/JP2006/30360 International Search Report.
PCT/JP2006/303260 International Search Report.
PCT/JP2006/303260 Written Opinion.
Extended European Search Report for PCT/JP2006/303260 mailed Aug. 16, 2010.
Chinese Office Action issued Apr. 19, 2011.

* cited by examiner

*Primary Examiner* — Seung C Sohn
(74) *Attorney, Agent, or Firm* — Lowe, Hauptman, Ham & Berner, LLP

(57) ABSTRACT

An object is to provide a separated sensor capable of synchronizing a light transmitting unit with a light receiving unit, without using a control line.
There is provided a separated sensor including a light transmitting unit that transmits detection light to a monitoring area, and a light receiving unit that receives detection light transmitted by the light transmitting unit, the light transmitting unit and the light receiving unit laid out separately from each other. On one of the light transmitting unit and the light receiving unit, there is provided a synchronization-light transmitting unit that transmits, by wireless, synchronization light to synchronize the light transmitting unit with the light receiving unit. On the other of the light transmitting unit and the light receiving unit, there are provided a synchronization-light receiving unit that receives the synchronization light transmitted from the synchronization-light transmitting unit, and a synchronization-establishment processing unit that performs a predetermined process to establish the synchronization based on the synchronization light received by the synchronization-light receiving unit.

9 Claims, 17 Drawing Sheets

SEPARATE-TYPE DETECTOR WITH REDUNDANT SYNCHRONIZATION FEATURE

RELATED APPLICATIONS

The present application is based on, and claims priority from, International Application Number PCT/JP2006/303260, filed Feb. 23, 2006, the disclosure of which is hereby incorporated by reference herein in its entirety.

TECHNICAL FIELD

The present invention relates to a separated sensor that senses various objects to be monitored, such as fire and a human body in a monitoring area.

BACKGROUND ART

There has been conventionally known a light-extinction-type smoke sensor that senses smoke based on an extinction rate of detection light, as one mode of a smoke sensor that senses smoke generated by fire or the like. Among these light-extinction-type smoke sensors, as a sensor capable of monitoring a relatively wide area, there is a photoelectric separated smoke sensor.

FIG. 18 is a system configuration diagram of a conventional photoelectric separated smoke sensor. The photoelectric separated smoke sensor 100 includes light transmitting units 101A to 101C that transmit detection light, and light receiving units 102A to 102C that receive the detection light, by oppositely laying out these units with a distance sandwiching a monitoring area between these units. The light receiving units 102A to 102C laid out oppositely to the light transmitting units 01A to 101C, respectively receive the detection light transmitted from the light transmitting units 101A to 101C, respectively. The light receiving units 102A to 102C calculate a light extinction amount and a light extinction rate of the detection light, respectively. When the light extinction amount becomes equal to or larger than a predetermined reference value, the light receiving units 102A to 102C determine that smoke is generated (fire occurs), and output accident-warning audible signals indicating the occurrence of fire, to a receiving device 104 connected by wire through a control line 103.

To properly determine the light extinction amount of the detection light, the transmission timing of the detection light transmitted by the light transmitting units 101A to 101C needs to be synchronized with the reception timing of the detection light received by the light receiving units 102A to 102C. For this purpose, conventionally, the light transmitting units 101A to 101C and the light receiving units 102A to 102C are connected to each other by wire using the control line 105. The light transmitting units 101A to 101C output control signals (synchronization signals) to the light receiving units 102A to 102C via the control line 105. The light receiving units 102A to 102C receive the light at a predetermined interval based on a synchronization timing specified by the synchronization signals, thereby establishing the synchronization between the light transmitting units 101A to 101C and the light receiving units 102A to 102C (for example, see Patent Document 1).

Patent Document 1: Japanese Patent Application Laid-open No. H08-227489

DISCLOSURE OF THE INVENTION

Problems to be Solved by the Invention

However, according to the conventional method of establishing synchronization of the separated sensor, the control line to perform the synchronization needs to be established. Therefore, the work process of installing the sensor increases, and the cost of installing the control line is necessary. This installation cost increases when the distance between the light transmitting unit and the light receiving unit increases, and also increases when the number of installing the light transmitting unit and the light receiving unit increases. In recent years, the use of a high-quality cable for the control line is legally obliged by the fire code and the like. In this case, the installation cost of the control line further increases.

The present invention has been achieved in view of the above problems, and an object of the present invention is to provide a separated sensor capable of performing synchronization between the light transmitting unit and the light receiving unit, without using a control line.

Means for Solving Problems

Accordingly, according to one aspect of the present invention, there is provided a separated sensor including a transmitting unit that transmits detection light to a monitoring area, and a light receiving unit that receives the detection light transmitted by the light transmitting unit, with both units laid out separately from each other. One of the light transmitting unit and the light receiving unit is provided with a synchronization-light transmitting unit that transmits synchronization light by wireless to synchronize the light transmitting unit with the light receiving unit. The other of the light transmitting unit and the light receiving unit is provided with a synchronization-light receiving unit that receives the synchronization light transmitted from the synchronization-light transmitting unit, and a synchronization-establishment processing unit that performs a predetermined process to establish the synchronization based on the synchronization light received by the synchronization receiving unit.

Effect of the Invention

According to the present invention, any one of the light transmitting unit and the light receiving unit transmits synchronization light, and the other one of the units receives the synchronization light, thereby establishing synchronization. Therefore, the synchronization signal does not need to be transmitted by connecting between the light transmitting unit and the light receiving unit with the control line. Consequently, the installation of the control line can be omitted. As a result, the installation of the separated sensor becomes easy, and the installation cost can be reduced.

EXPLANATIONS OF REFERENCE NUMERALS

Figure 1:
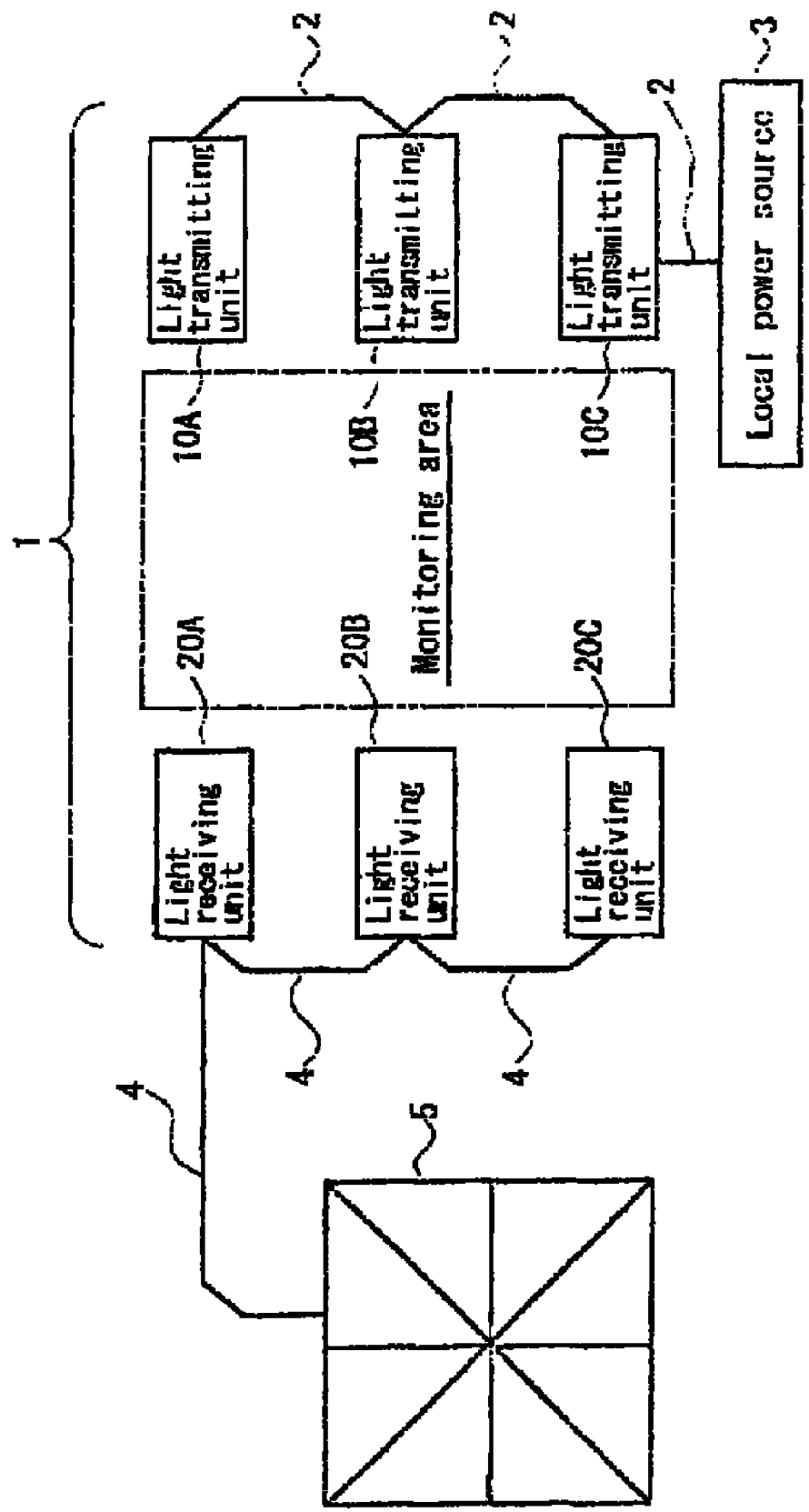
FIG. 1 is a system configuration diagram of a sensor according to a first embodiment.

1, 6, 100 Sensor
2 Power supply line
3 Local power source
4, 103, 105 Control line
5, 104 Receiving device
10, 10A to 10C, 101A to 101C Light transmitting unit
11 Casing
12 Light source
13 Memory unit
14 Light-transmission control unit
20, 20A to 20C, 30, 102A to 102C Light receiving unit
21 Casing
22 Light receiving element
23 Amplifier
24 A/D converter
25 Peak holding unit
26 Memory unit
27 Synchronization instruction switch
28 Light-reception control unit
28a, 31a Light-extinction-amount calculating unit
28b, 31b Smoke determining unit
28c, 31c Synchronization establishing unit
28d, 31d Synchronization correcting unit

BEST MODES FOR CARRYING OUT THE INVENTION

Preferred embodiments for carrying out the present invention will be explained below in detail with reference to the accompanying drawings. After explaining [I] basic concept common to all embodiments, [II] detailed contents of each embodiment are explained, and lastly [III] modified examples for each embodiment are explained. Note that the present invention is not limited to the embodiments.

[I] Basic Concept Common to all Embodiments

First, the basic concept common to all embodiments is explained. Each embodiment relates to a separated sensor. The separated sensor relates to a separated sensor that senses various objects to be monitored such as fire and a human body in a monitoring area.

While detailed contents of the monitoring area monitored by the separated sensor are arbitrary, particularly, a relatively wide space such as a gymnasium, a warehouse, and a shopping mall can be the monitoring area, by separately laying out the light transmitting unit and the light receiving unit oppositely to each other. While detailed contents of the objects to be monitored by the separated sensor are arbitrary, the separated sensor can be structured as, for example, a fire sensor that detects fire, or can be structured as a human sensor that detects a human body. In the following explanations, a photoelectric separated smoke sensor is taken up as an example that determines presence or absence of smoke based on the amount of detection light extinguished by smoke, the detection light transmitted by the light transmitting unit and received by the light receiving unit.

According to this separated sensor, the light transmitting unit and the light receiving unit are synchronized by wireless. That is, the light transmitting unit transmits synchronization light as an optical signal, and the light receiving unit receives this signal, thereby establishing synchronization. Therefore, a control line for the synchronization signal does not need to be established between the light transmitting unit and the light receiving unit. Consequently, the installation work of the separated sensor can be improved, and its installation cost can be reduced.

For the synchronization light, the detection light used to detect smoke can be also used as the synchronization light, in addition to transmitting and receiving the light exclusively used for synchronization. When the detection light used to detect smoke is used, a constituent element to transmit and receive exclusive light is not necessary. Therefore, the separated sensor can be configured more easily. In the following embodiments, the use of the detection light as the synchronization light is explained, and, unless otherwise specified, the detection light and the synchronization light are simply referred to as a detection light, without discriminating between the two lights.

For the transmission-and-reception pattern of the synchronization light, various patterns can be listed up. In each embodiment, a synchronization pattern capable of finishing in short time the transmission and reception of light and waves between the light transmitting unit and the light receiving unit is used in wirelessly establishing the synchronization. Based on this arrangement, electric power required to transmit and receive light is decreased.

[II] Detailed Contents of Each Embodiment

Next, detailed contents of each embodiment are explained.

First, a first embodiment of the present invention is explained. The first embodiment relates to a mode of intermittently transmitting detection light by only a predetermined light-transmission time at each predetermined light transmission interval, and intermittently receiving the detection light by only a predetermined light receiving time at each predetermined light reception interval different from the light transmission interval.

First, a configuration of a photoelectric separated smoke sensor (hereinafter, "sensor") is explained. FIG. 1 is a system configuration diagram of the sensor according to the first embodiment. The sensor 1 includes light transmitting units 10A to 10C and light receiving units 20A to 20C. The light transmitting units 10A to 10C and the light receiving units 20A to 20C are separately laid out with a distance of about several tens to several hundreds of millimeters therebetween, and facing each other by sandwiching a monitoring area. The light transmitting units 10A to 10C transmit detection light to detect smoke respectively, and the light receiving unit 20A receives detection light from the light transmitting unit 10A, the light receiving unit 20B receives detection light from the light transmitting unit 10B, and the light receiving unit 20C receives detection light from the light transmitting unit 10C. The light transmitting units 10A to 10C are similarly configured, and the light receiving units 20A to 20C are similarly configured. Therefore, in the following explanations, the light transmitting units 10A to 10C are called light transmitting units 10, and the light receiving units 20A to 20C are called light receiving units 20.

Each light transmitting unit 10 transmits detection light. Each light transmitting unit 10 is connected to a local power source 3 via a power supply line 2, and is driven by the electric power supplied from the local power source 3. However, when each light transmitting unit 10 incorporates a battery, the power supply line 2 and the local power source 3 can be omitted. Alternatively, the electric power can be supplied to each light transmitting unit 10 via each light receiving unit 20.

Each light receiving unit 20 receives detection light. Each light receiving unit 20 is connected to a receiving device 5 via a control line 4. Upon receiving a power supply from the receiving device 5 via the control line 4, when the light receiving unit 20 detects smoke (or when the light receiving unit 20 determines that fire occurs, based on a detection result of smoke), the light receiving unit 20 outputs an accident-warning audible signal showing this effect to the receiving device 5 via the control line 4. Upon receiving the accident-warning audible signal from the light receiving unit 20, the receiving device 5 performs a predetermined alarm operation. The alarm operation includes the outputting of alarm sound, and outputting of a signal transmission signal to other disaster prevention device (not shown) to notify the device about a detection of smoke or fire.

Figure 2:
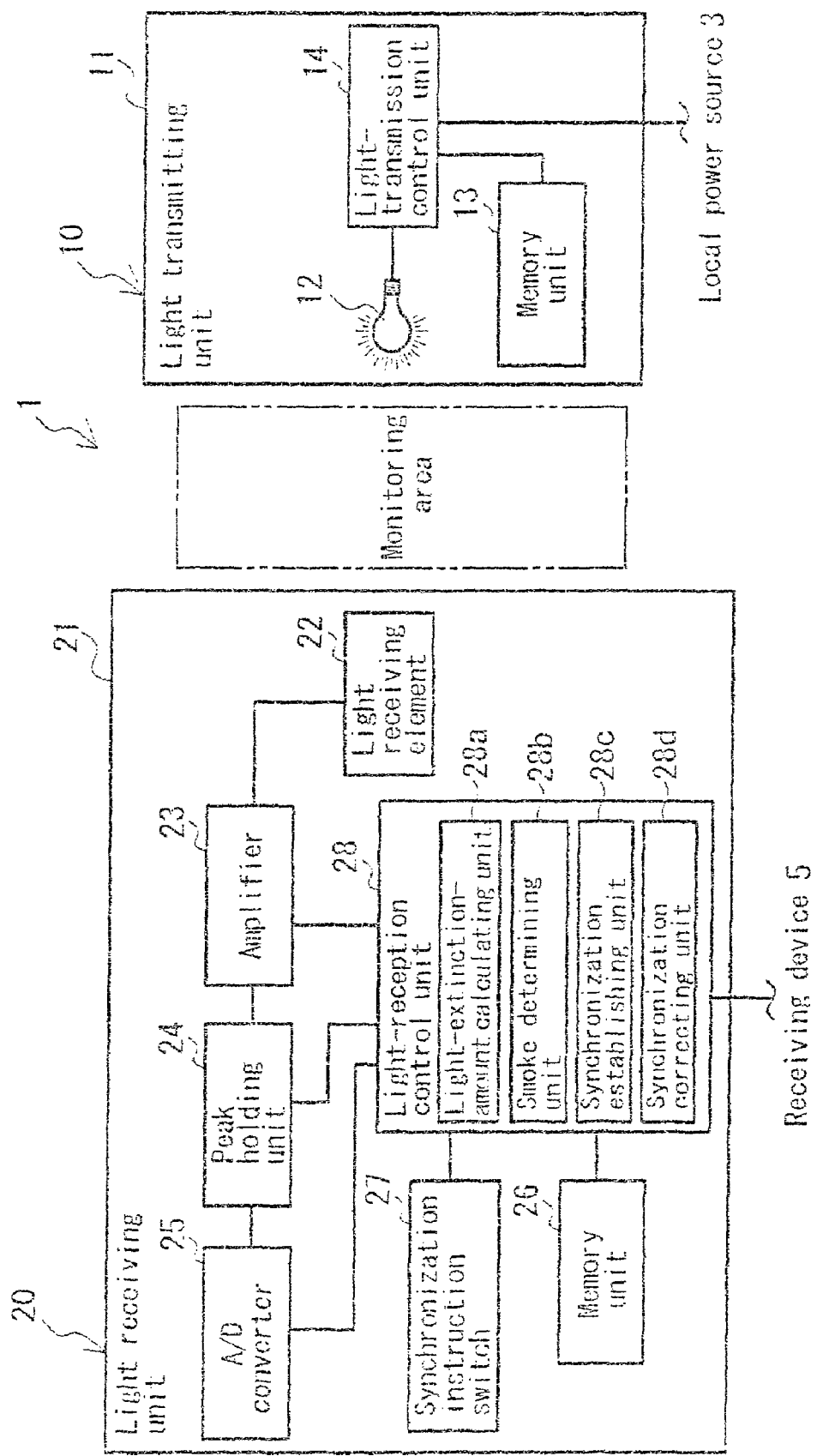
FIG. 2 is a block diagram conceptually showing main electric configurations of a light transmitting unit and a light receiving unit.

FIG. 2 is a block diagram schematically showing main electric configurations of the light transmitting unit 10 and the light receiving unit 20. The light transmitting unit 10 includes a light source 12, a memory unit 13, and a light-transmission control unit 14 within a casing 11. While a detailed configuration of the light source 12 is arbitrary, an LED (Light Emitting Diode) and an incandescent lamp can be used, for example. In the first embodiment, this detection light is used as synchronization light for establishing synchronization. Therefore, the light source 12 transmits synchronization light wireless, and corresponds to a synchronization-light transmitting unit in the claims. The memory unit 13 is a unit that stores information such as programs and various parameters necessary for the light transmitting unit 10 to perform the light transmission operation, and includes an EEPROM (Electronically Erasable and Programmable Read Only Memory) and a RAM (Random Access Memory), for example. The memory unit 13 stores a light transmission interval and a light transmission time as information, for example. The light-transmission control unit 14 controls light transmission performed by the light source 12, and transmits the detection light to the monitoring area by blinking the light source 12.

On the other hand, the light receiving unit 20 receives the detection light, and includes a light receiving element 22, an amplifier 23, a peak holding unit 24, an A/D converter 25, a memory unit 26, a synchronization instruction switch 27, and a light-reception control unit 28, within a casing 21.

The light receiving element 22 receives the detection light, and outputs a voltage or a current corresponding to the light reception amount. While a detailed configuration of the light receiving element 22 is arbitrary, a photodiode can be used, for example. As described above, in the first embodiment, because the detection light is used as the synchronization light for establishing the synchronization, the light receiving element 22 receives the synchronization light, and corresponds to a synchronization-light receiving unit in the claims.

The amplifier 23 is an amplifying unit that amplifies the output of the light receiving element 22. The amplifier 23 is turned ON or OFF by a control signal from a synchronization establishing unit described later.

The peak holding unit 24 receives an analog output amplified by the amplifier 23, detects and holds (peak hold) a maximum value of the output voltage during the reception of the output, and outputs an analog signal of a voltage corresponding to this maximum value.

The A/D converter 25 converts the analog output that is output from the peak holding unit 24, by each predetermined number of times in a predetermined A/D conversion interval.

The memory unit 26 is a unit that stores information such as programs and various parameters necessary for the light receiving unit 20 to perform the light reception operation, and includes an EEPROM (Electronically Erasable and Programmable Read Only Memory) and a RAM (Random Access Memory), for example. The memory unit 26 stores a threshold value used for a smoke determining unit 28b described later to determine smoke, and a synchronization establishing flag, a light reception interval, a light receiving time, a second light-receiving time, and a synchronization correction interval that are referenced by the synchronization establishing unit described later.

The synchronization instruction switch 27 is an instruction unit that is used by an operator to instruct the starting of a synchronization establishing operation. It is assumed here that the synchronization instruction switch 27 is configured as a cover switch automatically pressed when a casing cover (not shown) provided in the casing of the light receiving unit 20 is closed.

The light-reception control unit 28 is a processing unit that performs various processes in the light receiving unit 20, and includes an IC (Integrated Circuit) and a process program operating on this IC, for example. While detailed processing content performed by the light-reception control unit 28 is described later, the light-reception control unit 28 includes, as functional concept, a light-extinction-amount calculating unit 28a, a smoke determining unit 28b, a synchronization establishing unit 28c, and a synchronization correcting unit 28d. The light-extinction-amount calculating unit 28a calculates a light extinction amount of the detection light received by the light receiving element 22. The smoke determining unit 28b determines presence or absence of smoke (or presence or absence of the occurrence of fire) in the monitoring area based on the light extinction amount calculated by the light-extinction-amount calculating unit 28a. The smoke determining unit 28b compares the light extinction amount with a predetermined threshold value stored in the memory unit 26, and determines that smoke is generated when the light extinction amount exceeds the threshold value. The synchronization establishing unit 28c performs a predetermined process to establish synchronization based on the detection light received by the light receiving element 22, and corresponds to a synchronization-establishment processing unit in the claims. The synchronization correcting unit 28d corrects the synchronization timing, at a point of time when a predetermined correction interval passes, after establishing the synchronization, and corresponds to a synchronization-correction processing unit in the claims.

Figure 3:
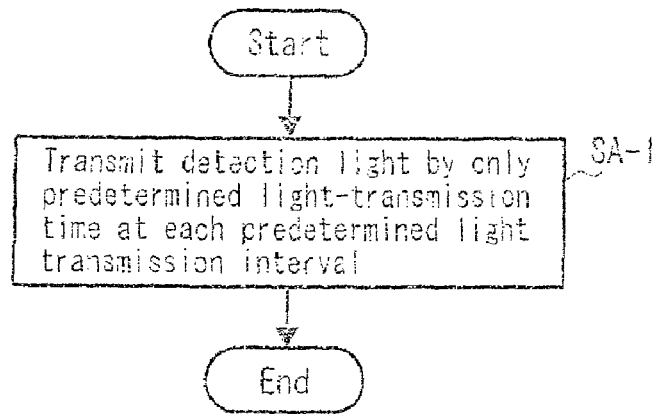
FIG. 3 is a flowchart of a startup process performed by the light transmitting unit.

Next, the process of starting up the sensor 1 to the monitoring state is explained. First, the startup process of the light transmitting unit 10 is explained. FIG. 3 is a flowchart of the startup process of the light transmitting unit 10. When an operator turns on the power source of the light transmitting unit 10 in a predetermined method, a light-transmission control unit 14 of the light transmitting unit 10 performs the startup process. In this startup process, the light-transmission control unit 14 calls the light transmission interval and the light transmission time from the memory unit 13, and controls the light source 12 based on this light transmission interval, thereby transmitting the detection light by a predetermined transmission time at each light transmission interval (step SA-1). While detailed contents of the light transmission interval and the light transmission time are arbitrary, the light transmission interval is set to 1 to 10 seconds, and the light transmission time is set to 1 pulse, for example. The startup process of the light transmitting unit 10 is finished in the above.

Figure 4:
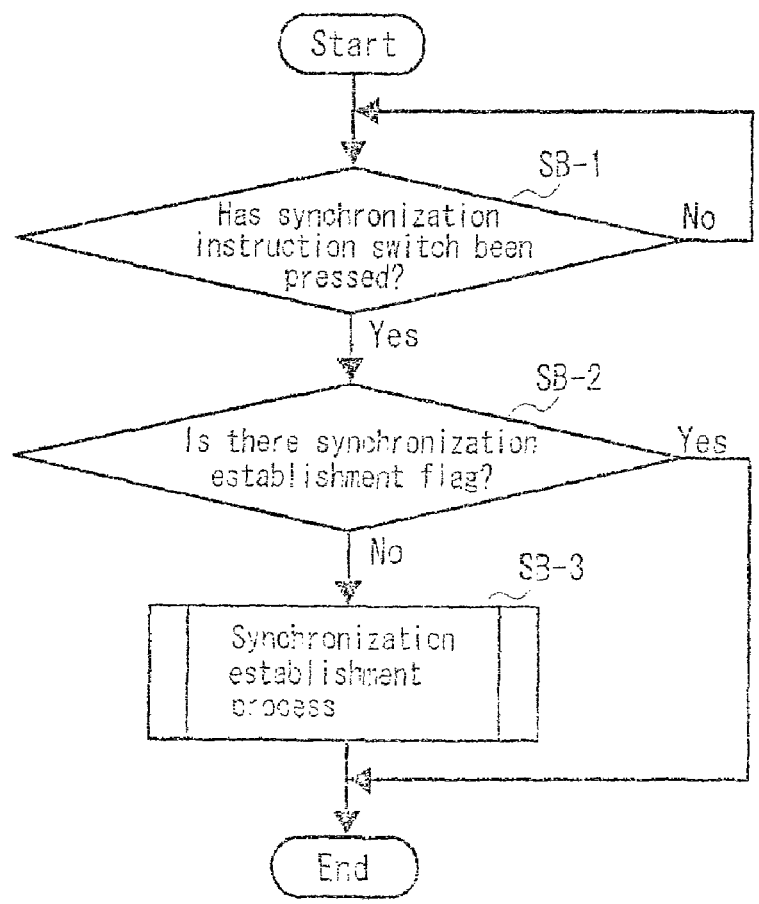
FIG. 4 is a flowchart of a startup process performed by the light receiving unit.

Next, the startup process performed by the light receiving unit 20 is explained. FIG. 4 is a flowchart of the startup process performed by the light receiving unit 20. When the operator turns on the power source of the light receiving unit 20 in a predetermined method, the light-reception control unit 28 of the light receiving unit 20 waits until the synchronization instruction switch 27 is pressed (step SB-1). For example, at the time of initializing the sensor 1, the operator turns on the power source of the light receiving unit 20 in a predetermined method, adjusts the light axis of the detection light between the light transmitting unit 10 and the light receiving unit 20 in a predetermined method, and closes a casing cover of the light receiving unit 20. When the casing cover is closed in this way, the synchronization instruction switch 27 of the light receiving unit 20 is automatically pressed following this operation. When the power source of the already-installed light receiving unit 20 is disconnected, the operator turns on the power source of the light receiving unit 20 to restart the light receiving unit 20. In this case, the adjustment of the light axis is already finished, and the casing cover of the light receiving unit 20 is already closed. Therefore, the synchronization instruction switch 27 is always in the pressed state.

When the synchronization instruction switch 27 is in the pressed state (step SB-1, Yes), the light-reception control unit 28 determines whether a synchronization establishment flag is stored in the memory unit 26 (step SB-2). When the synchronization establishment flag is stored (step SB-2, Yes), synchronization is already established, and it is determined that a synchronization establishment process does not need to be additionally performed, thereby finishing the startup process without performing the synchronization establishment process. The state shifts to the normal monitoring state using the synchronization condition stored in the memory unit 26. On the other hand, when the synchronization establishment flag is not stored (step SB-2, No), synchronization is not yet established, and it is determined that synchronization establishment needs to be performed, thereby performing the synchronization establishment process (step SB-3). After finishing the synchronization establishment process, the state is shifted to the normal monitoring state using a synchronization condition specified by the synchronization establishment process. The startup process of the light receiving unit 20 is finished in the above.

Figure 5:
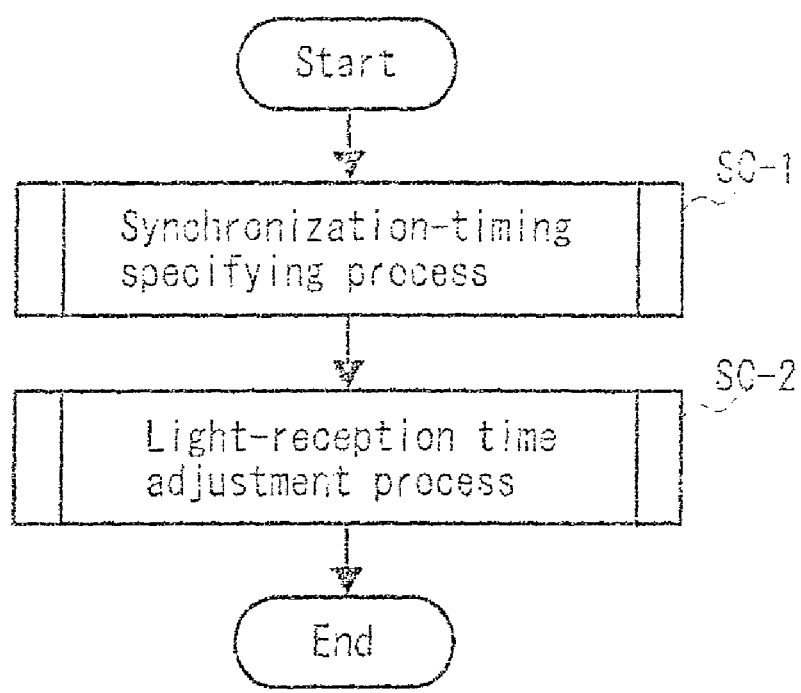
FIG. 5 is a flowchart of a synchronization establishment process performed by the light receiving unit.

Next, the synchronization establishment process performed by the light receiving unit 20 at step SB-3 is explained. FIG. 5 is a flowchart of the synchronization establishment process performed by the light receiving unit 20. This synchronization establishment process is divided into a synchronization-timing specifying process for specifying the synchronization timing (step SC-1), and a light-reception-time adjustment process for shortening the light reception time around the synchronization timing specified in this synchronization-timing specifying process (step SC-2).

Figure 6:
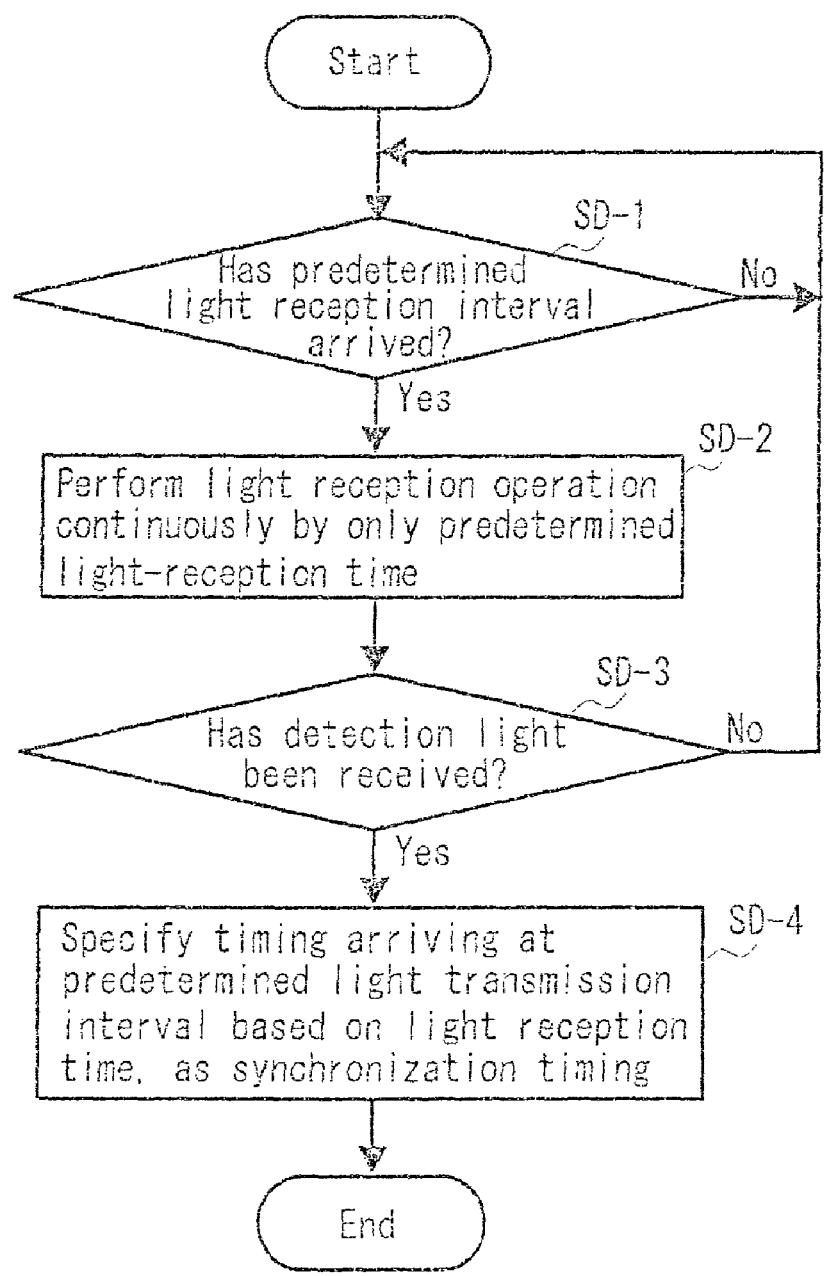
FIG. 6 is a flowchart showing the basic concept of a synchronization-timing specifying process of the light receiving unit.
Figure 7:
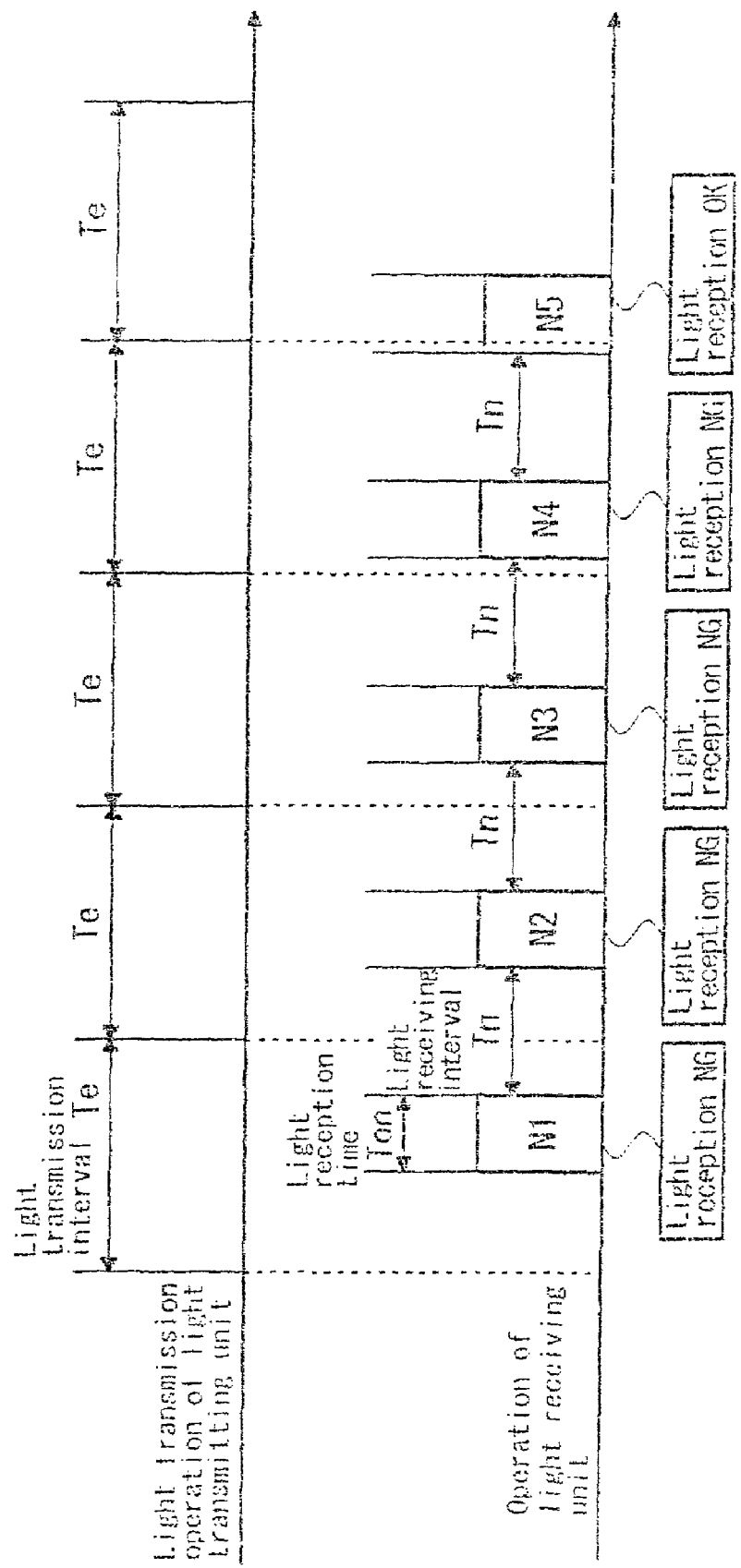
FIG. 7 is a timing chart showing the timing of a light transmission operation performed by the light transmitting unit and a light reception operation performed by the light receiving unit in the synchronization-timing specifying process.

First, the basic concept of the synchronization-timing specifying process at step SC-1 is explained. FIG. 6 is a flowchart showing the basic concept of the synchronization-timing specifying process of the light receiving unit 20. FIG. 7 is a timing chart showing the timing of the light transmission operation performed by the light transmitting unit 10 and the light reception operation performed by the light receiving unit 20 in the synchronization-timing specifying process. As shown in FIG. 7, the light-transmission control unit 14 of the light transmitting unit 10 transmits light during only a predetermined light transmission time at each predetermined light transmission interval Te after the startup process as described above.

On the other hand, as shown in FIGS. 6 and 7, the synchronization establishing unit 28c of the light receiving unit 20 performs a predetermined light reception operation for receiving the detection light at each predetermined light reception interval different from the light transmission interval (step SD-1). By performing the light reception operation at the light reception interval different from the light transmission interval in this way, the detection light can be received at the timing corresponding to a common multiple of the light transmission interval and the light reception interval, even when intermittently performing the light transmission and the light reception. Particularly, in the first embodiment, the light reception interval is set shorter than the light transmission interval (the light reception interval<the light transmission interval). For example, when the light transmission interval is 3 seconds, the light reception is performed at one to two-second interval. This is for the following reason. That is, in the first embodiment, it is assumed that the light transmission interval is maintained in the same interval even in the smoke monitoring state after the synchronization establishment. Therefore, the light transmission interval needs to be a proper interval to perform smoke sensing. Preferably, to decrease power consumption in the light transmitting unit 10, the light transmission interval to perform smoke sensing is set relatively long in the range having no trouble in the smoke sensing. On the other hand, when light reception is performed at a longer interval than the light transmission interval, there is a high risk that the synchronization establishment time becomes longer, and therefore, this is not preferable. Therefore, in the first embodiment, the light transmission interval is set as a relatively long interval suitable for the smoke sensing, and in the meantime, the light reception time is set shorter than the light transmission interval, thereby speeding up establishment of the synchronization.

The synchronization establishing unit 28c determines presence of continuous reception of the detection light during a predetermined light reception time in each light reception operation (step SD-2). That is, the synchronization establishing unit 28c compares the output from the light receiving element 22 (actually, a conversion value obtained by the A/D converter 25 as described later) with a predetermined value in each light reception operation, thereby determining presence of reception of the detection light (step SD-3). For example, when the light transmission interval is 3 seconds, light reception operation is continuously performed by several hundreds of milliseconds in each light reception operation. FIG. 7 shows an example in which the light reception is performed five times from N1 to N5. When the synchronization establishing unit 28c determines that the detection light is received during any one of the light reception operations (step SD-3, Yes), the synchronization establishing unit 28c specifies the timing that arrives at a predetermined synchronization interval (the same as the light transmission interval, in this case) based on this light reception time, as a synchronization timing (step SD-4). For example, in FIG. 7, the detection light can be received for the first time at the fifth light reception operation N5. Therefore, the synchronization timing is specified based on the light reception time in the light reception operation N5. The synchronization timing specifying process is finished in the above. The initial light reception interval and light reception time can be stored in a referable manner in the memory unit 26 or can be built in as an internal parameter of a synchronization-establishment process program, before the shipment of the sensor 1 from the plant (this is similarly applied to a second light-reception time and other time data described below).

Figure 8:
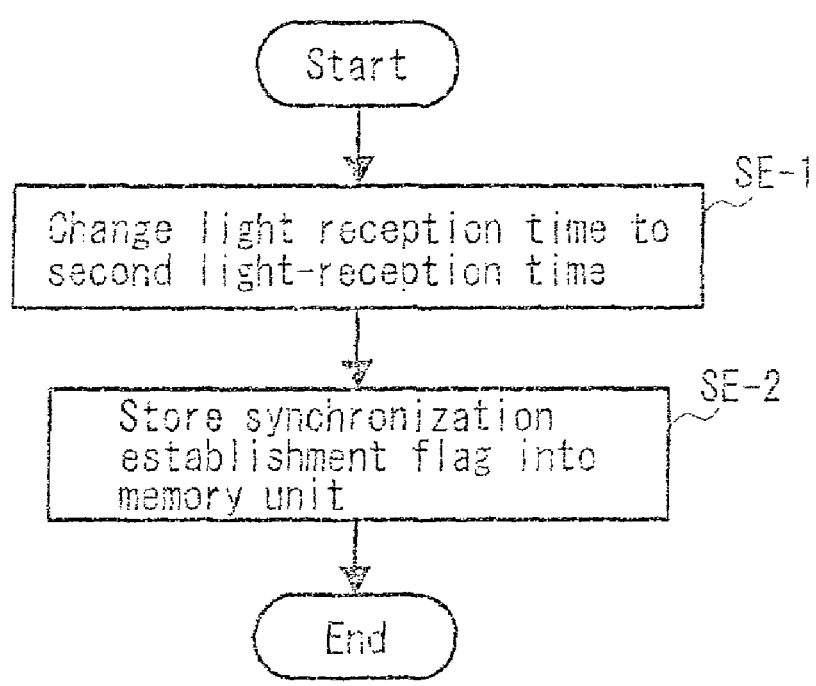
FIG. 8 is a flowchart showing the basic concept of a light-reception-time adjustment process performed by the light receiving unit.
Figure 9:
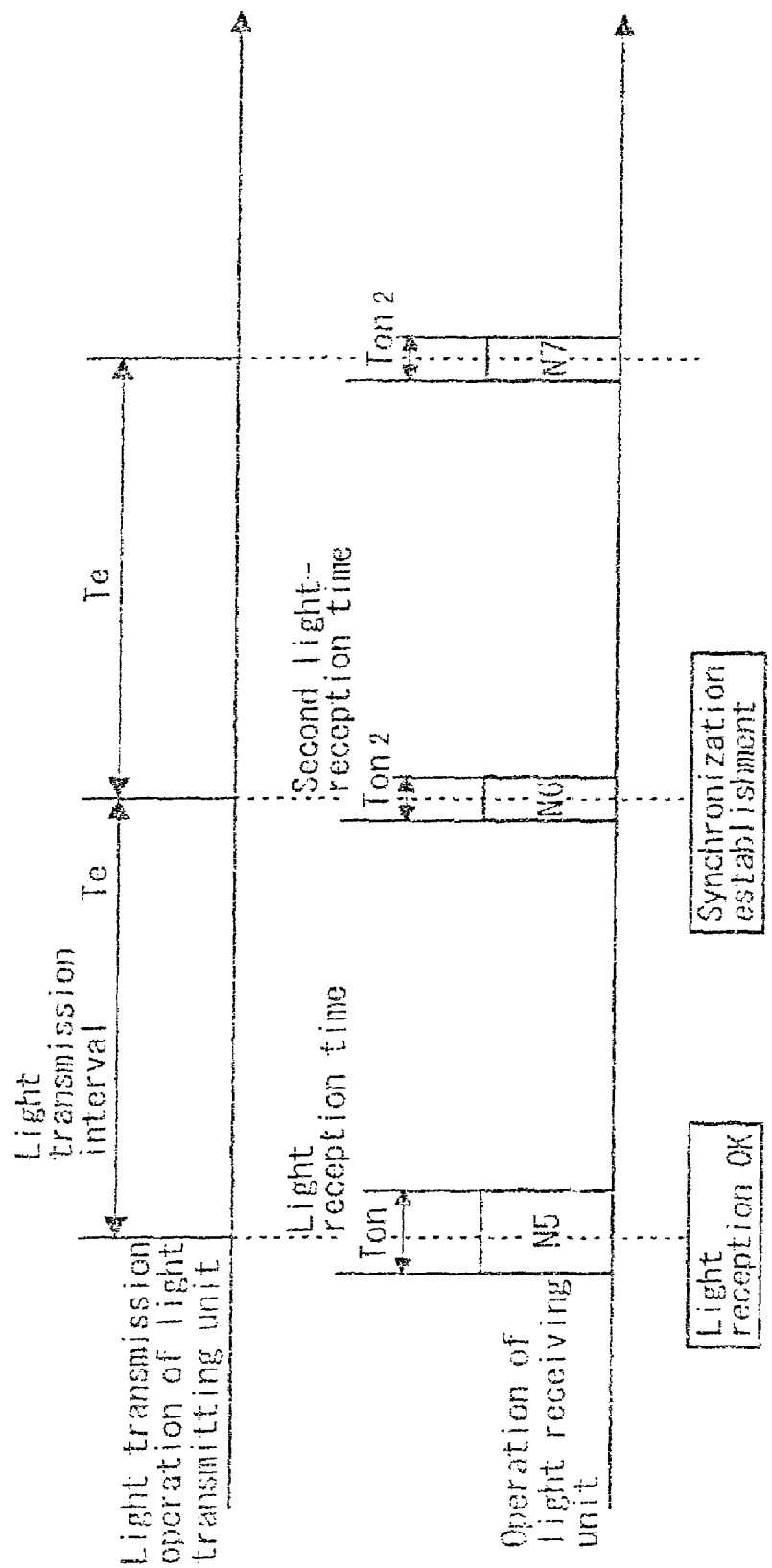
FIG. 9 is a timing chart showing the timing of the light transmission operation performed by the light transmitting unit and the light reception operation performed by the light receiving unit in the light-reception-time adjustment process.

The basic concept of the light-reception-time adjustment process at step SC-2 shown in FIG. 5 is explained next. FIG. 8 is a flowchart showing the basic concept of the light-reception-time adjustment process performed by the light receiving unit 20, and FIG. 9 is a timing chart showing the timing of the light transmission operation performed by the light transmitting unit 10 and the light reception operation performed by the light receiving unit 20 in the light-reception-time adjustment process. As shown in FIG. 9, the synchronization establishing unit 28c changes the continuous light-reception time of the detection light to a predetermined second light-reception time shorter than the prior light-reception time, around the synchronization timing specified in the synchronization-timing specifying process (step SE-1). FIG. 9 shows light reception operations at three times from N5 to N7 (the light reception operation N5 is the same as the light reception operation N5 in FIG. 7). In this example, the light reception time in the light reception operation N6 is changed to the second light-reception time. For example, when the prior light-reception time is several hundreds of milliseconds, the second light-reception time is set to several tens of milliseconds. Thereafter, the synchronization establishing unit 28c stores the synchronization establishment flag into the memory unit 26 (step SE-2). The light-reception-time adjustment process is finished in the above, and the synchronization establishment process ends.

In the subsequent normal monitoring state, the light receiving unit 20 receives the detection light at the synchronization timing specified in the synchronization-timing specifying process, and by the second light-reception time changed in the light-reception-time adjustment process, thereby synchronizing the light transmission timing of the light transmitting unit 10 with the light reception timing of the light receiving unit 20. The synchronization establishment flag stored in the memory unit 26 is erased when the power source of the light receiving unit 20 is disconnected. Therefore, when the power source is turned on again, the synchronization establishment process is started automatically subject to the pressing of the synchronization instruction switch 27, as explained above in the startup process.

Effects of the synchronization establishment process are as follows. As a simple method of establishing synchronization by wireless, there is considered the following. The light transmitting unit 10 transmits detection light at a predetermined light transmission interval, and the light receiving unit 20 continuously receives light during a longer time than the light transmission interval, thereby establishing synchronization timing based on the timing when the detection light is received. However, in continuously receiving light over a long time in this way, power consumption of an amplifier that amplifies the output from the light receiving element 22 increases, in the light receiving unit 20. To solve this inconvenience, in the synchronization-timing specifying process, the light receiving unit 20 intermittently receives light at a shorter light reception interval than the light transmission interval, thereby decreasing the power consumption of the light receiving unit 20.

When intermittently receiving light as described above, probability of being able to receive the detection light can be improved and synchronization can be quickly established, when the light reception time in each light reception operation is increased. However, when the length of the light reception time is maintained as it is after establishing the synchronization, time during which the detection light is not actually received in each light reception operation increases, and power consumption of the light receiving unit 20 wastefully increases. To solve this inconvenience, in the light-reception-time adjustment process, the light reception time is set relatively long until when synchronization is established, and after the synchronization establishment, the light reception time is changed to a short time as far as possible (that is, the second light-reception time) when the detection light can be received at the synchronization timing. With this arrangement, efficiency of power consumption of the light receiving unit 20 is improved.

Figure 10:
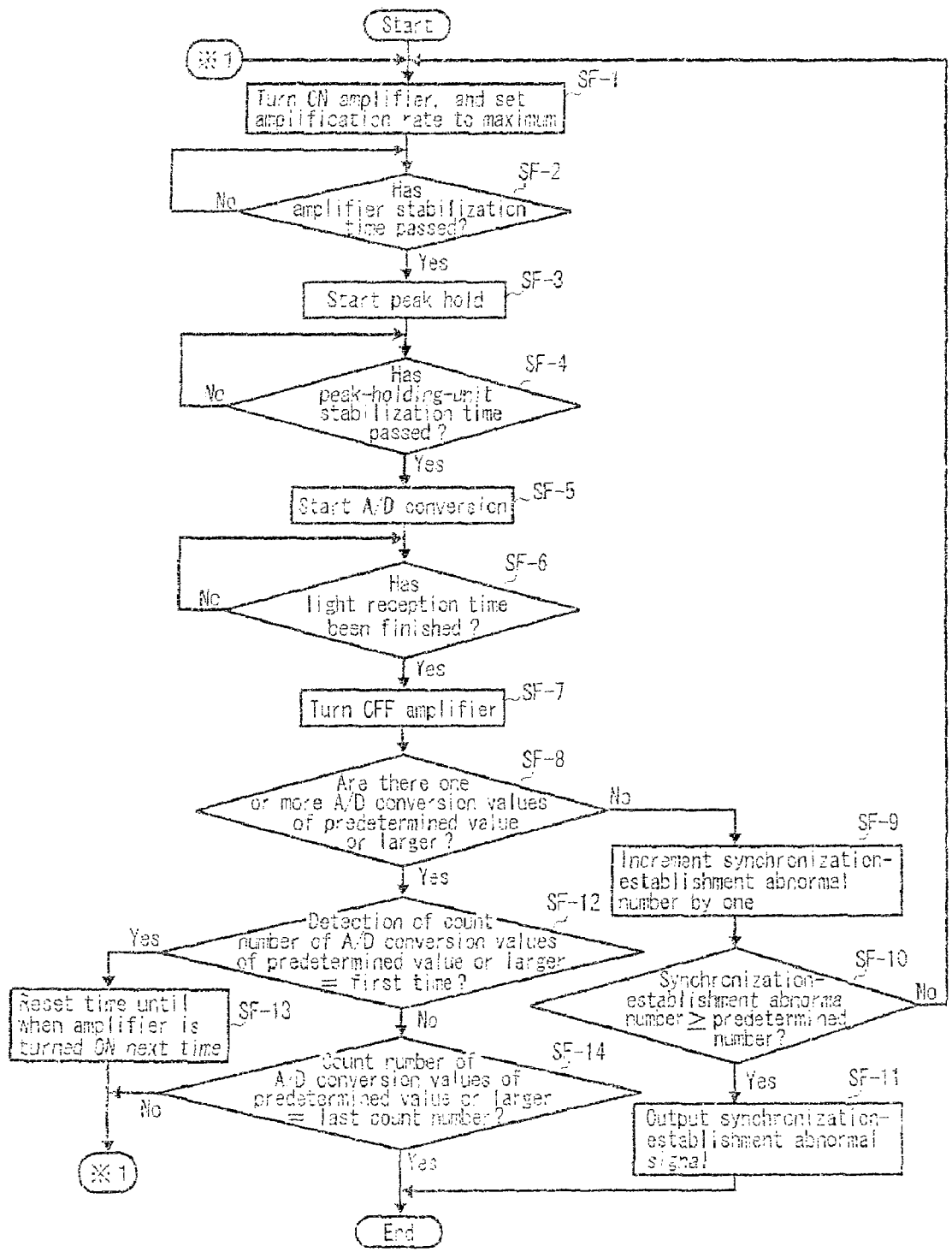
FIG. 10 is a flowchart showing details of the synchronization-timing specifying process.
Figure 11:
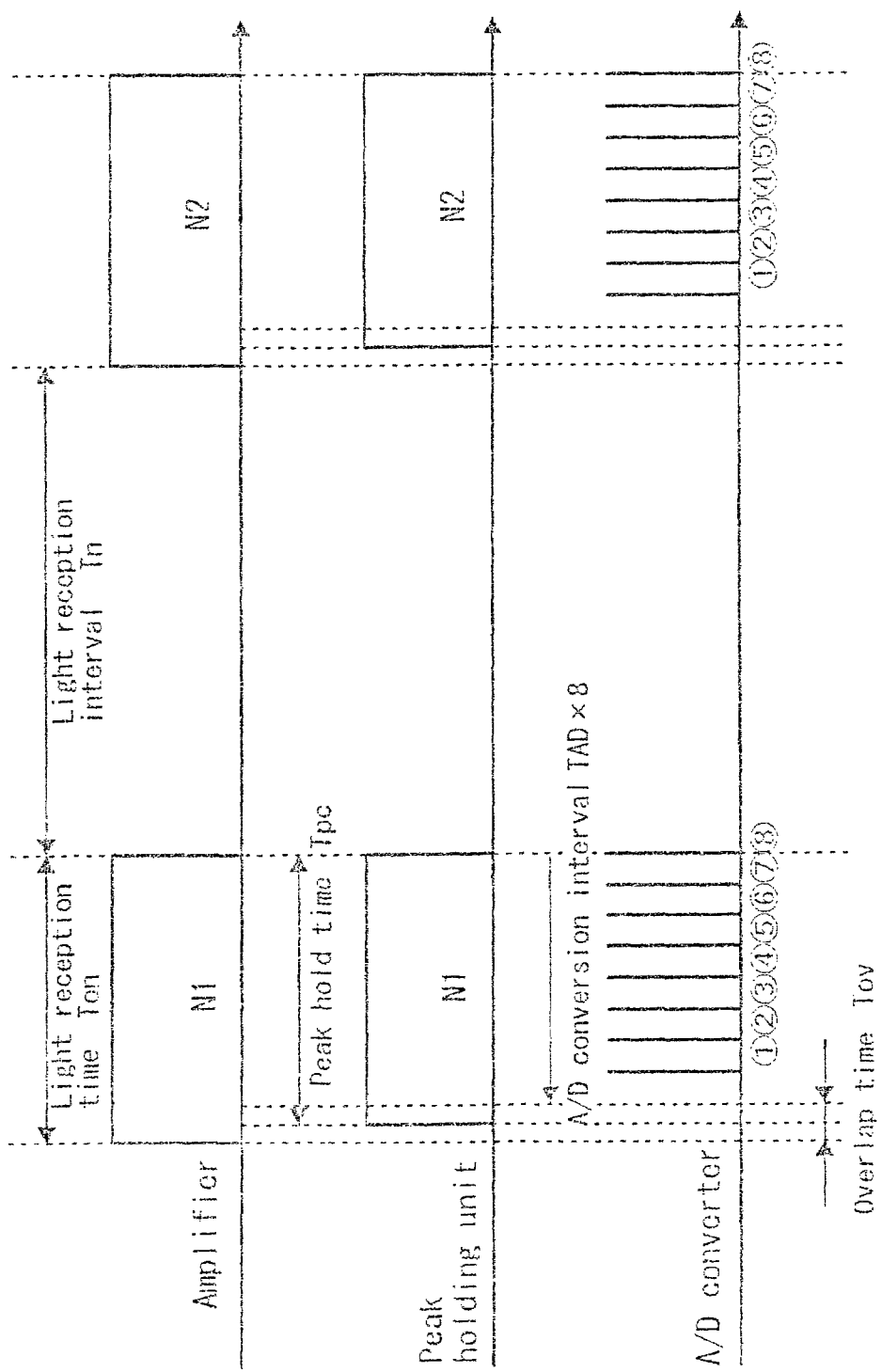
FIG. 11 is a timing chart showing details of the operation timing of each unit of the light receiving unit in the synchronization-timing specifying process.

Next, the synchronization establishment process performed as described above by the light receiving unit 20 is explained in further detail. First, details of the synchronization-timing specifying process are explained. FIG. 10 is a flowchart showing the details of the synchronization-timing specifying process, and FIG. 11 is a timing chart showing the details of the operation timing of each unit of the light receiving unit 20 in the synchronization-timing specifying process.

The synchronization establishing unit 28c of the light receiving unit 20 turns ON the amplifier 23 and maximizes the amplification rate (step SF-1), and waits for a predetermined time until when the amplifier 23 is electrically stabilized (hereinafter, "amplifier stabilization time") (step SF-2). After the lapse of the amplifier stabilization time, the synchronization establishing unit 28c starts the peak hold of the output of the amplifier 23 by the peak holding unit 24 (step SF-3), and waits for the lapse of a predetermined time until when the output of the peak holding unit 24 is electrically stabilized (hereinafter, "peak-holding-unit stabilization time") (step SF-4). Detailed numerical values of the amplifier stabilization time and the peak-holding-unit stabilization time can be different depending on specifications of the amplifier 23 and the peak holding unit 24. The detailed numerical values are stored in the memory unit 26 in advance, and the synchronization establishing unit 28c references these values according to need.

After the stabilization time of the peak holding unit 24, the synchronization establishing unit 28c makes the A/D converter 25 A/D convert the output from the peak holding unit 24 (step SF-5). This A/D conversion is performed by a predetermined number of times at a predetermined A/D conversion interval. Next, the synchronization establishing unit 28c continuously turns ON the amplifier 23 for only a light reception time Ton (step SF-6, Yes), and turns OFF the amplifier 23 (step SF-7). The synchronization establishing unit 28c determines whether there is one or more A/D conversion values of a predetermined value or larger (whether there is an A/D conversion value of a predetermined value or larger), out of the A/D conversion values obtained by the A/D conversion performed by the A/D converter 25 (step SF-8). For this predetermined value, for example, a lowest value at which the detection light transmitted from the light transmitting unit 10 can be determined as being received is set.

When it is determined that there is no A/D conversion value of a predetermined value or larger (step SF-8, No), the synchronization establishing unit 28c cannot receive the detection light from the light transmitting unit 10, determines that there is a possibility that a certain abnormal state interfering the synchronization establishment is generated, and increments by one a synchronization-establishment abnormal number (initial value=0) stored in the memory unit (step SF-9). The synchronization establishing unit 28c determines whether this synchronization-establishment abnormal number becomes equal to or larger than a predetermined number (for example, 10 to 20 times) at which it can be determined that abnormality has occurred in the synchronization establishment (step SF-10). When the synchronization-establishment abnormal number has not become the predetermined number or larger (step SF-10, No), the synchronization establishing unit 28c returns to step SF-1 and repeats the light reception operation to continue the synchronization establishment process. Thereafter, when the synchronization-establishment abnormal number becomes equal to or lager than the predetermined number (step SF-10, Yes), the synchronization establishing unit 28c determines that abnormality occurred in the synchronization establishment, outputs a synchronization-establishment abnormal signal to the receiving device 5 (step SF-11), and finishes the synchronization establishment process. The receiving device 5 receives this synchronization-establishment abnormal signal, and displays or outputs voice to indicate that the synchronization establishment abnormality occurs, thereby notifying the operator about this abnormal state.

In this way, the synchronization establishing unit 28c repeatedly performs the process from steps SF-1 to SF-10 until when it is determined that there is one or more A/D conversion values of a predetermined value or larger or until when the synchronization-establishment abnormal number becomes equal to or larger than the predetermined number. Each timing of the light reception operation in the process at steps SF-1 to SF-10 can be determined as follows. First, as shown in FIG. 11, a sum of the amplifier stabilization time and the peak-holding-unit stabilization time is expressed as an overlap time Tov, a time for the peak holding unit 24 to perform peak hold is expressed as a peak hold time Tpc, an interval of A/D conversion performed by the A/D converter 25 is expressed as an A/D conversion interval TAD, and a light reception interval (a time from when the amplifier 23 is turned ON until when the amplifier 23 is turned ON next) is expressed as a light reception interval Tn.

In the first embodiment, the A/D conversion is performed eight times during each light reception operation in the synchronization-timing establishment process. Therefore, the overlap time Tov can be expressed as follows.

Overlap time $Tov$=Light reception time $Ton$−(A/D conversion interval $TAD$×8)

In the first embodiment, during the one-time light transmission interval, the light transmission time Ton is included twice, and the time of turning ON the amplifier 23 is shortened by the overlap time Tov coming in the second light-reception time Ton. With this arrangement, during the reception of the detection light, the outputs from the amplifier 23 and the peak holding unit 24 are already stabilized. Therefore, the light reception interval Tn can be expressed as follows.

Light reception interval $Tn$=Light transmission interval+Overlap time $Tov$−(2×Light reception time $Ton$)

The process at steps SF-1 to SF-10 is repeatedly performed at this timing. When it is determined at step SF-8 that there is one or more A/D conversion values of a predetermined value or larger (step SF-8, Yes), there is a possibility that the detection light can be received during the light reception operation. Therefore, in this case, the timing when this A/D change value is obtained can be set as a reference of the synchronization timing. However, there is also a possibility that noise light other than the detection light is received. Accordingly, in this case, it is determined whether the detection light is also received at the same timing in the next light reception operation, and only when the detection light is received at the same timing, the timing when this A/D change value is obtained is set as the reference of the synchronization timing. Specifically, the synchronization establishing unit 28c counts the number of times when the A/D conversion values equal to or larger than the predetermined value are obtained. This number of times can be determined by storing the number of times when the A/D conversion values equal to or larger than the predetermined value are obtained, into the memory unit 26. The synchronization establishing unit 28c determines whether the number of times is the first time (step SF-12), and when the number is the first time (when the A/D conversion value of a predetermined value or larger is first obtained. Step SF-12, Yes), the light reception interval Tn is set again to confirm whether the detection light can be received during the light reception operation (step SF-13), and the process returns to step SF-1 to confirm the light reception again.

Light reception interval $Tn$=Light transmission interval−light reception time $Ton$ With this arrangement, the A/D conversion can be performed at the same timing as that of the prior light reception operation during which the detection light is received.

On the other hand, when the number of times when the A/D conversion values of a predetermined value or larger is not the first time (when the A/D conversion values of a predetermined value or larger can be obtained at two times or more. Step SF-12, No), the number of the A/D conversion values of a predetermined value or larger is counted, and is stored in the memory unit. It is determined whether this count number is the same as the count number stored in the memory unit at the preceding step SF-8 (step SF-14).

When the count number of the A/D conversion values of a predetermined value or larger is not the same as the preceding count number (step SF-14, No), the synchronization establishing unit 28c determines that the light reception timing of the detection light during the light reception operation is not the same, and that it cannot be determined yet that the synchronization is normally performed. The process returns to step SF-1, and the synchronization establishing unit 28c performs the synchronization establishment process from the beginning again.

On the other hand, when the count value of the A/D conversion values of a predetermined value or larger is the same as the preceding count value (step SF-14, Yes. This count value is hereinafter called a coincided count number), the synchronization-timing specifying process is finished, and the process shifts to the next light-reception-time adjustment process.

Figure 12:
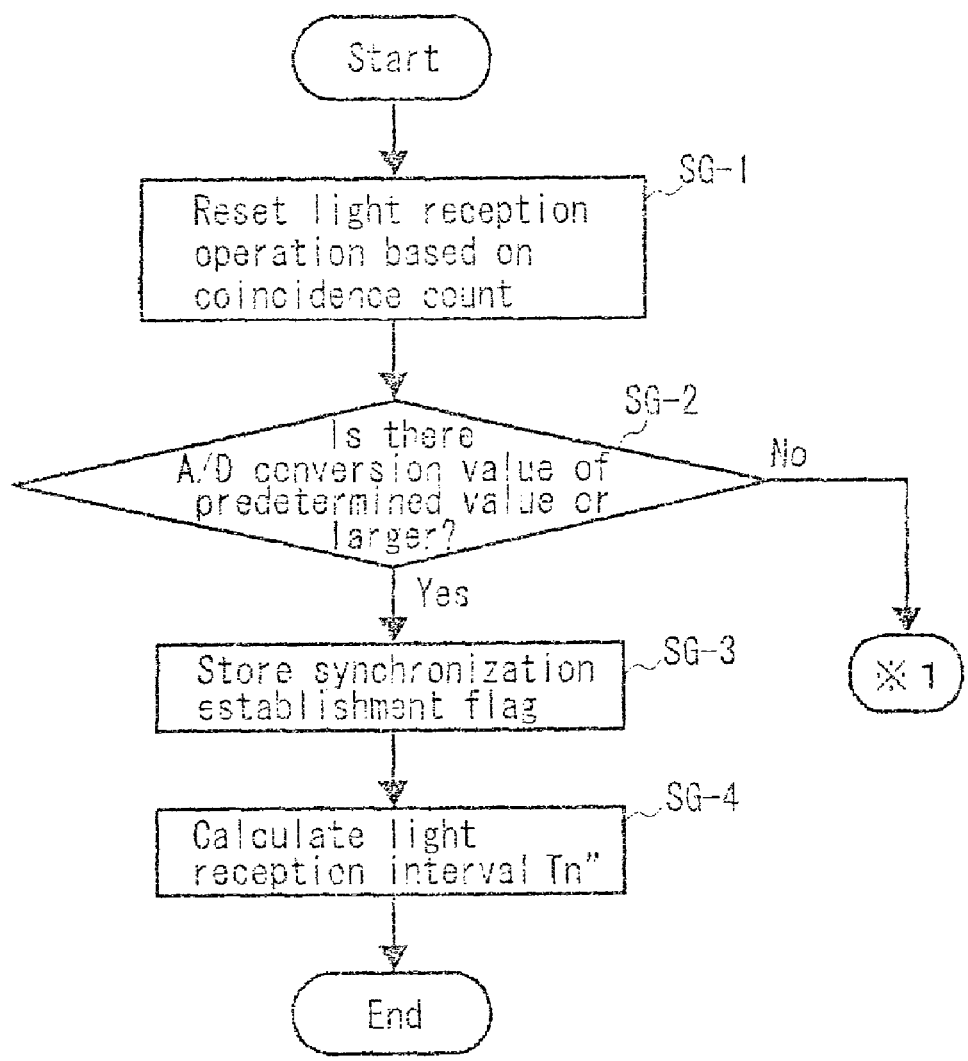
FIG. 12 is a flowchart showing details of the light-reception-time adjustment process.
Figure 13:
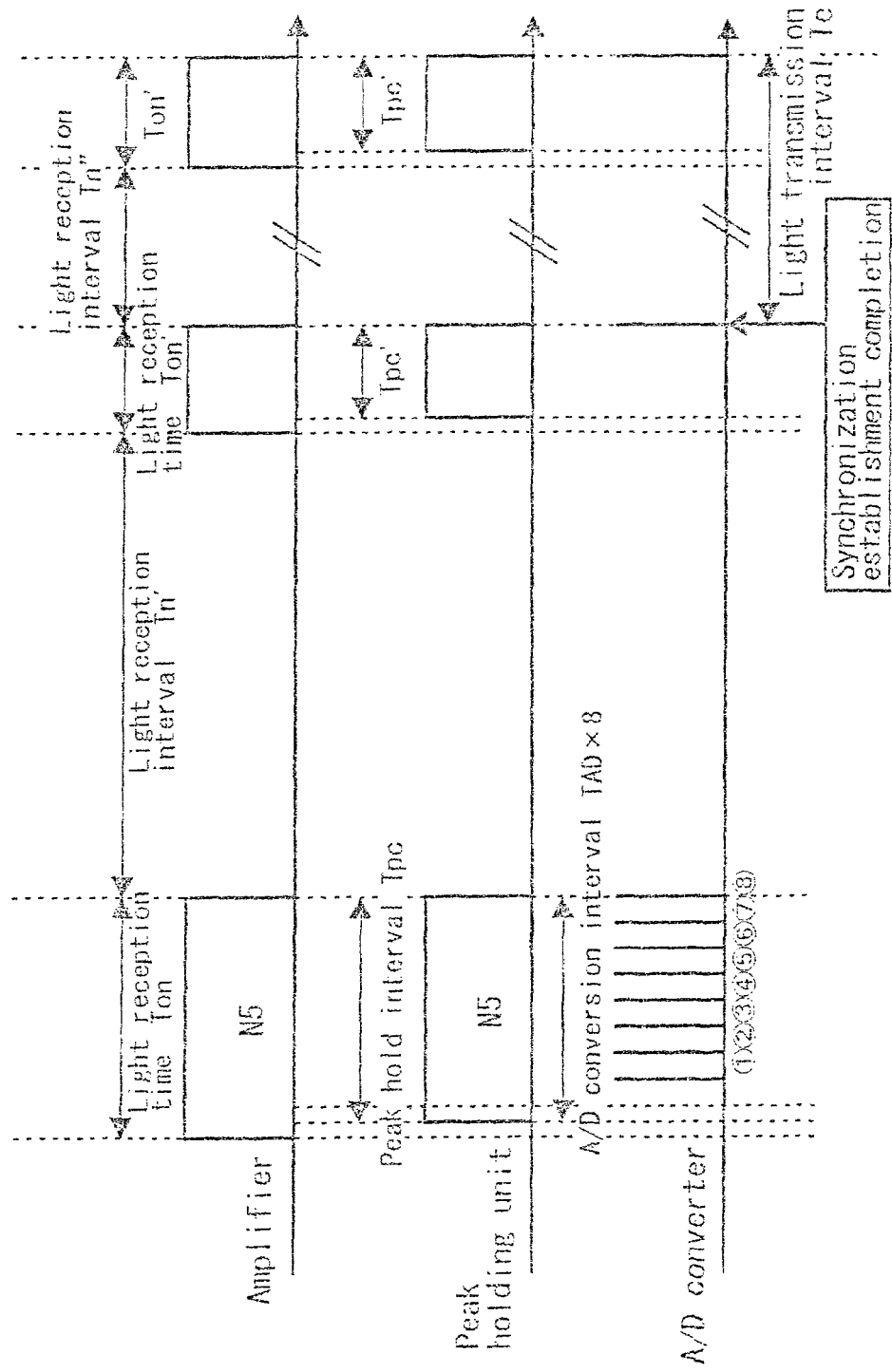
FIG. 13 is a timing chart showing details of the operation timing of each unit of the light receiving unit in the light-reception-time adjustment process.

Next, details of the light-reception-time adjustment process are explained. FIG. 12 is a flowchart showing the details of the light-reception-time adjustment process, and FIG. 13 is a timing chart showing the details of the operation timing of each unit of the light receiving unit 20 in the light-reception-time adjustment process. In this light-reception-time adjustment process, the light reception time is adjusted using the coincided count number of the synchronization-timing specifying process shown in FIG. 10. That is, at which point of time in the light reception operation the light reception is performed in the synchronization-timing specifying process can be specified, based on this coincided count number. Therefore, based on this time point, the light reception time is adjusted to the second light-reception time shorter than the synchronization-timing specifying process.

Specifically, the synchronization establishing unit 28c resets a light reception interval Tn', a light reception time Ton', and a peak hold time Tpc' in the subsequent light reception operation as follows, based on the coincided count number (step SG-1).

Light reception interval $Tn'$=Light transmission interval$-(Tov+Tx)-TAD\times$(coincided count number$-1$)

Light reception time $Ton'=Tov+Tx+TAD+Tx$

Peak hold time $Tpc'=Ton'-$Amplifier stabilization time

In the above, Tx represents an estimate time (hereinafter, "synchronization-deviation estimate time) of a deviation of synchronization" (hereinafter, "synchronization deviation") that can occur between the light transmitting unit 10 and the light receiving unit 20 until when a cycle correction process described later is performed. This synchronization-deviation estimate time is set to a large value when accuracy of a timer that counts a predetermined light transmission interval is low or when the time until when the cycle correction process is performed is long in the light transmitting unit 10 or the light receiving unit 20.

Among the above numerical values, basically, the light reception interval Tn' is calculated by subtracting the overlap time Tov' from the light transmission interval. In this example, the synchronization-deviation estimate time is further subtracted, thereby turning ON the amplifier 23 by bringing forward the synchronization deviation time. With this arrangement, even when the synchronization deviation occurs, the detection light can be received, and reliability of smoke sensing is increased. When the count number of the A/D conversion values of a predetermined value or larger is large, the detection light is detected at the early time during the light reception operation. Therefore, an A/D conversion time-interval is subtracted by the number corresponding to the count number so that the light reception timing is brought forward by this count number. The reason why 1 is subtracted from the count number is that when the count number is 1, the detection light is received at the last of the light reception time Ton'. By subtracting the A/D conversion interval TAD, the timing of turning ON the amplifier 23 does not need to be brought forward. The light reception time Ton' is basically calculated by adding the overlap time Tov to a minimum time during which the detection light can be received (in this example, one-time A/D conversion interval TAD). In this example, a synchronization-deviation estimate time Tx is added by two times. With this arrangement, either when the reception of the detection light is brought forward due to the occurrence of the synchronization deviation or when the reception of the detection light is delayed due to the occurrence of the synchronization deviation, the detection light can be received and the reliability of the smoke sensing is increased. The peak hold time Tpc' is calculated by subtracting the amplifier stabilization time from the light reception time Ton'.

Next, the synchronization establishing unit 28c confirms whether the light reception operation after the resetting functions validly. Specifically, in the light reception operation after the resetting, the synchronization establishing unit 28c determines whether the A/D conversion values of a predetermined value or larger are obtained (step SG-2). When the A/D conversion values of a predetermined value or larger are not obtained (step SG-2, No), the process returns to the step SF-1 of the synchronization-timing specifying process in FIG. 10, and the synchronization establishing unit 28c performs the synchronization establishment process from the beginning again. On the other hand, when the A/D conversion values of a predetermined value or larger are obtained (step SG-2, Yes), it is determined that the light reception operation after the resetting functions validly (at this timing, the synchronization with the light transmitting unit 10 is obtained, and the detection light can be received properly), and the synchronization establishing unit 28c stores the synchronization establishment flag into the memory unit 16 (step SG-3).

Thereafter, the synchronization establishing unit 28c calculates a light reception interval Tn" as follows (step SG-4).

$Tn''$=Light transmission interval$-$light reception interval $Ton'$

The synchronization establishing unit 28c sets the amplification rate of the amplifier 23 to a predetermined amplification rate of the normal monitoring time smaller than the maximum amplification rate (step SG-5), and finishes the light-reception-time adjustment process. Thereafter, each time when the light reception interval Tn" arrives, the synchronization establishing unit 28c turns ON the amplifier 23 during only the light reception time Ton', thereby performing the light reception operation synchronized with the light transmitting unit 10.

Figure 14:
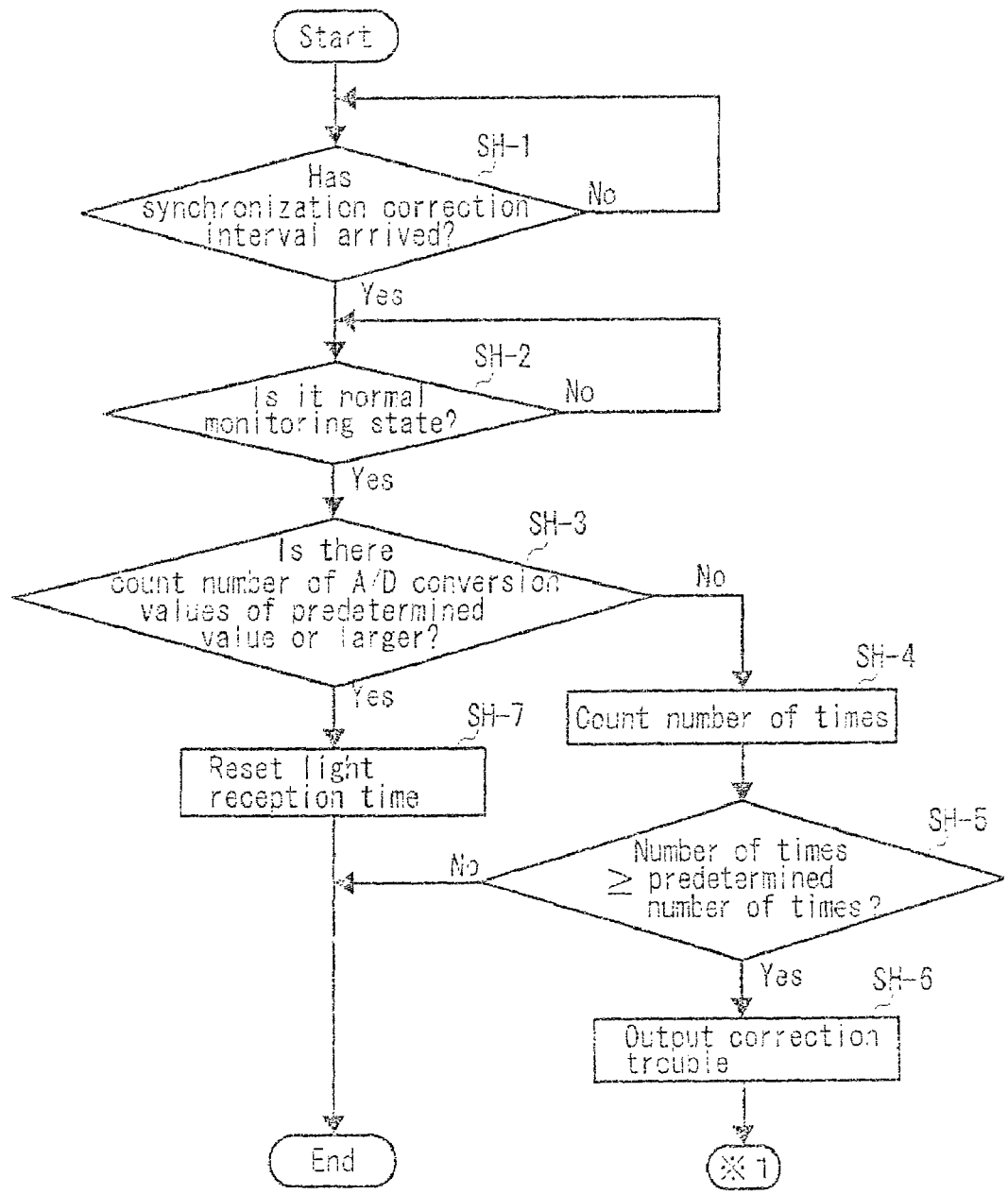
FIG. 14 is a flowchart of a synchronization correction process.
Figure 15:
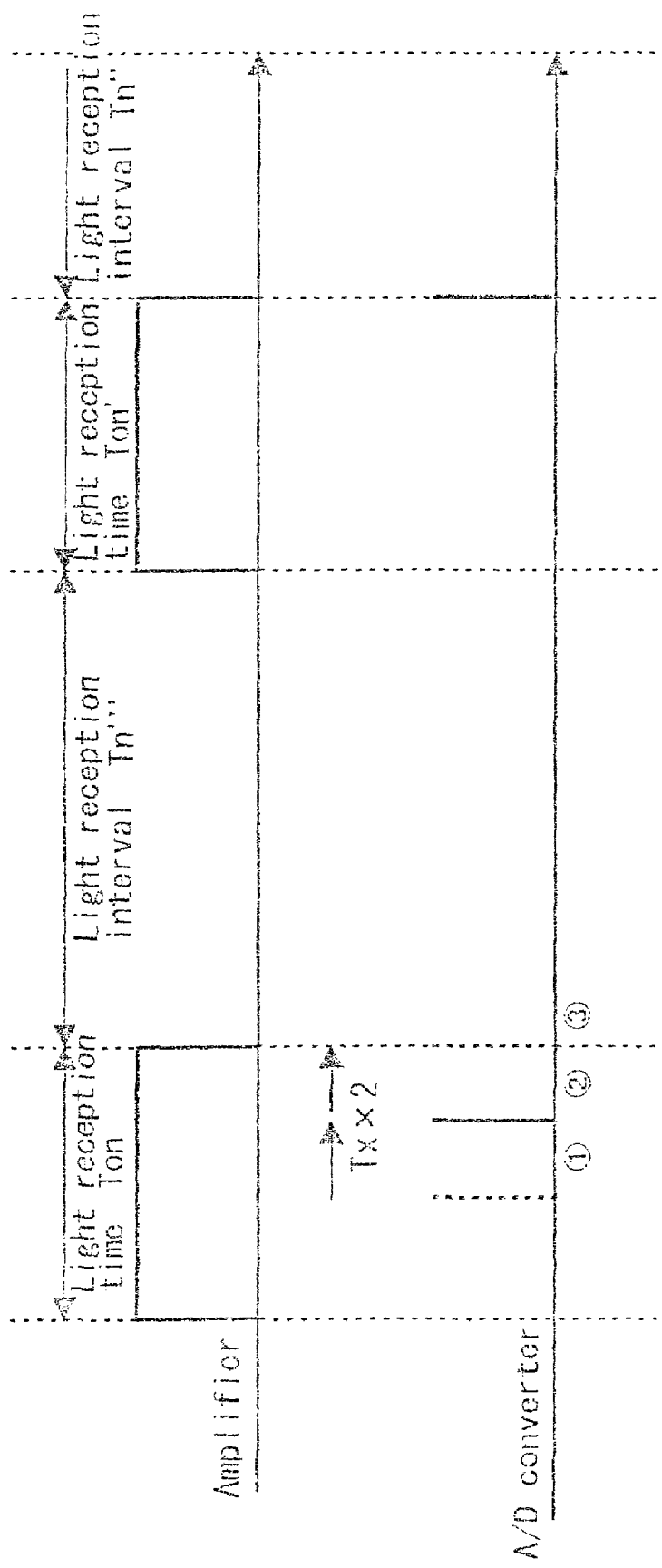
FIG. 15 is a timing chart showing details of the operation timing of each unit of the light receiving unit in the synchronization correction process.

The synchronization correction process is explained next. FIG. 14 is a flowchart of the synchronization correction process, and FIG. 15 is a timing chart showing the details of the operation timing of each unit of the light receiving unit 20 in the synchronization correction process. In this synchronization correction process, the synchronization correcting unit 28d monitors whether a predetermined synchronization-correction interval stored in the memory unit 26 in advance has passed (step SH-1). This synchronization correction interval is set so that the synchronization correction process is performed before the synchronization deviation amount becomes large enough to interrupt the proper reception of the detection light even when a synchronization deviation occurs. A detailed period is determined short, for example, 5 to 10 minutes, when the time count accuracy of a clock circuit (not shown) that counts the light transmission interval in the light transmitting unit 10 or the time count accuracy of a clock circuit (not shown) that counts the light reception interval in the light receiving unit 20 becomes low.

When this synchronization correction interval has passed (step SH-1, Yes), the synchronization correcting unit 28d determines whether the sensor 1 is at a predetermined synchronization correctable level (an A/D value of a constant value or above) (step SH-2). Only when the sensor 1 is in the normal monitoring state, the process shifts to the next step SH-3, and when the sensor 1 is not in the normal monitoring state, the process shifts to the next step SH-3 after waiting for a return to the normal monitoring state.

As states of not the normal monitoring state, there are a state that the sensor 1 detects smoke (fire), and a state that the occurrence of a trouble in the smoke sensor 1 is detected (for example, a state that the reception amount of the detection light decreases due to accumulation of dusts on the light axis of the detection light, and when this extinction amount becomes equal to or larger than a predetermined amount). The reason why the synchronization correction is not performed in the fire state or the trouble state is that, in this state, the light reception amount decreases due to the existence of smoke and dusts, and the synchronization correction process cannot be performed properly. A detailed determination of presence of the fire state or the trouble state is arbitrary. For example, in the fire state or the trouble state, the control unit of the light receiving unit 20 erects a predetermined flag in the memory unit 26, and the synchronization correcting unit 28d determines presence of the flag, thereby determining presence of the fire state or the trouble state. When an automatic compensation function that automatically increases the light reception amount to compensate for an extinction of the reception amount of the detection light due to the accumulation of dusts or the like is provided in the sensor 1, this automatic compensation function does not interrupt the synchronization correction process. Therefore, during the automatic compensation, the synchronization correction process is performed in a similar manner to that of the normal monitoring state. However, when the fire state or the trouble state does not interrupt the synchronization correction, the synchronization correction can be executed even in the fire state or the trouble state.

Thereafter, the synchronization correcting unit 28d determines whether there are one or more A/D conversion values of a predetermined value or larger among the A/D conversion values output from the A/D converter 25 (step SH-3). As the predetermined value, a threshold value of the extinction amount of the light reception amount to determine presence of smoke (a fire accident-warning determination threshold value) is used. When there is no A/D conversion value of a predetermined value or larger (step SH-3, No), the synchronization correcting unit 28d determines that the synchronization deviation amount exceeds a permissible limit of the synchronization correction, counts the number of times when the permissible limit is exceeded, and stores the count into the memory unit 26 (step SH-4). The synchronization correcting unit 28d compares the number of times with the predetermined number of times (step SH-5). When this number of times is not equal to or larger than the predetermined number of times (step SH-5, No), the synchronization correcting unit 28d determines that only a temporary trouble occurs, finishes the correction process without performing correction, and waits for the next correction process to be performed. On the other hand, when the number of times is equal to or larger than the predetermined number of times (step SH-5, Yes), the synchronization correcting unit 28d determines that there is a high possibility that more serious trouble occurs, and outputs a notice of the occurrence of the correction trouble to the light-reception control unit 28 (step SH-6). The light reception control unit 28 performs a predetermined process to notify the occurrence of the correction trouble to the user. For example, the light-reception control unit 28 outputs a correction trouble signal to the receiving device 5, and the receiving device 5 makes a trouble display light (not shown) blink. The synchronization correcting unit 28d reestablishes the synchronization, thereby making the synchronization establishing unit 28c start the synchronization establishment process to automatically solve the trouble. As a result, the synchronization-timing specifying process shown in FIG. 10 is started.

On the other hand, when there are one or more A/D conversion values of a predetermined value or larger at step SH-3 (step SH-3, Yes), the synchronization correcting unit 28d resets a light reception time Tn''' as follows using this count number, thereby correcting the synchronization (step SH-7). The synchronization correction process is finished in the above.

Light reception time $Tn'''$=(Light transmission interval light Reception interval $Ton'$)–(Synchronization-deviation estimate time $Tx$×(Count number–number of A/D conversion values of a predetermined value or larger counted during a normal time))

That is, when the number of A/D conversion values of a predetermined value or larger actually counted is larger than the number of A/D conversion values of a predetermined value or larger counted during the normal time (hereinafter, "reference count number"), there occurs a synchronization deviation between the transmission light and the reception light. Therefore, the synchronization timing is corrected by subtracting the synchronization-deviation estimate time Tx by the exceeded number. For example, when the reference count number is 2, the 2 is subtracted from the actual count number, and the synchronization-deviation estimate time Tx is subtracted by the number corresponding to this subtraction result. The reference count number can be arbitrarily set corresponding to the synchronization timing during the normal time. Preferably, the count number is set to the reference count number that can be corrected even when the actual synchronization timing is deviated forward or backward. For example, when the reference count number is 1, and also when the actual count number is smaller than 1, this deviation amount cannot be corrected any more. Therefore, preferably, the reference count number is set to about 2 to 3.

According to the first embodiment, the light transmitting unit 10 transmits detection light, and the light receiving unit 20 receives this detection light and establishes synchronization. Therefore, the light transmitting unit 10 and the light receiving unit 20 do not need to be connected together with the control line 4 to transmit the synchronization signal, and the installation of the control line 4 can be omitted. Consequently, the installation of the sensor 1 can be facilitated, and the installation cost can be reduced.

Because the detection light is used as the synchronization light, it is not necessary to provide a configuration element to transmit and receive light exclusive for the synchronization. The configuration of the sensor 1 can be simplified, and its manufacturing cost can be reduced.

Because the light reception interval is set shorter than the light transmission interval, the light transmission interval is set as a relatively long interval suitable for smoke sensing, and the light reception time can be set shorter than the light transmission interval to quickly perform synchronization establishment.

After the synchronization timing is specified, the reception time of the detection light is changed to the second light-reception time. Therefore, the synchronization establishment can be performed quickly using a relatively long light-reception time until the synchronization establishment. At the same time, light reception power can be decreased using a relatively short light-reception time after the synchronization establishment.

After the passing of the amplifier stabilization time, presence of reception of synchronization light is determined. Therefore, the amplifier 23 does not determine presence of reception of the synchronization light in an unstable state.

Consequently, presence of reception of the synchronization light can be determined more securely, and reliability of the synchronization establishment process can be improved.

In the synchronization establishment process, the amplifier 23 is set to a maximum amplification rate, and after the synchronization establishment, the amplifier 23 is reset to a predetermined amplification rate smaller than the maximum amplification rate. Therefore, in the synchronization establishment process, light reception performance of the synchronization light is maximized, and possibility of synchronization establishment can be improved.

Because the synchronization correcting unit 28d corrects the synchronization timing, the synchronization deviation can be canceled automatically, and the light receiving unit 20 can receive the detection light at a proper timing. Therefore, reliability of the smoke detection over a long period can be improved.

In the synchronization correction process, when the synchronization light of a light reception amount of a predetermined value or larger is not received, the synchronization establishment process by the synchronization establishing unit 28c is automatically started. With this arrangement, when there is a possibility that the synchronization deviation exceeds the limit of correction, the synchronization establishment can be automatically performed from the beginning again. Even when the synchronization deviation is large, the synchronization timing can be corrected to the proper state. Alternatively, by notifying the occurrence of the correction trouble to the user, the user can be urged to take action at an early timing.

In the synchronization correction process, when the synchronization light of a light reception amount of a predetermined value or larger is received, the synchronization deviation can be automatically canceled, and the light receiving unit 20 can receive the detection light at a proper timing, by setting, as a synchronization timing, the timing arriving at a predetermined light transmission interval based on the timing of receiving the synchronization light.

Second Embodiment

Detailed contents of a second embodiment are explained next. The second embodiment relates to a mode of intermittently performing the synchronization establishment process at a predetermined light reception interval longer than the light transmission interval. Note that, unless otherwise specified, the configuration is similar to that of the first embodiment, and the same constituent elements as those of the first embodiment are denoted by like reference numerals used in the first embodiment according to need.

Figure 16:
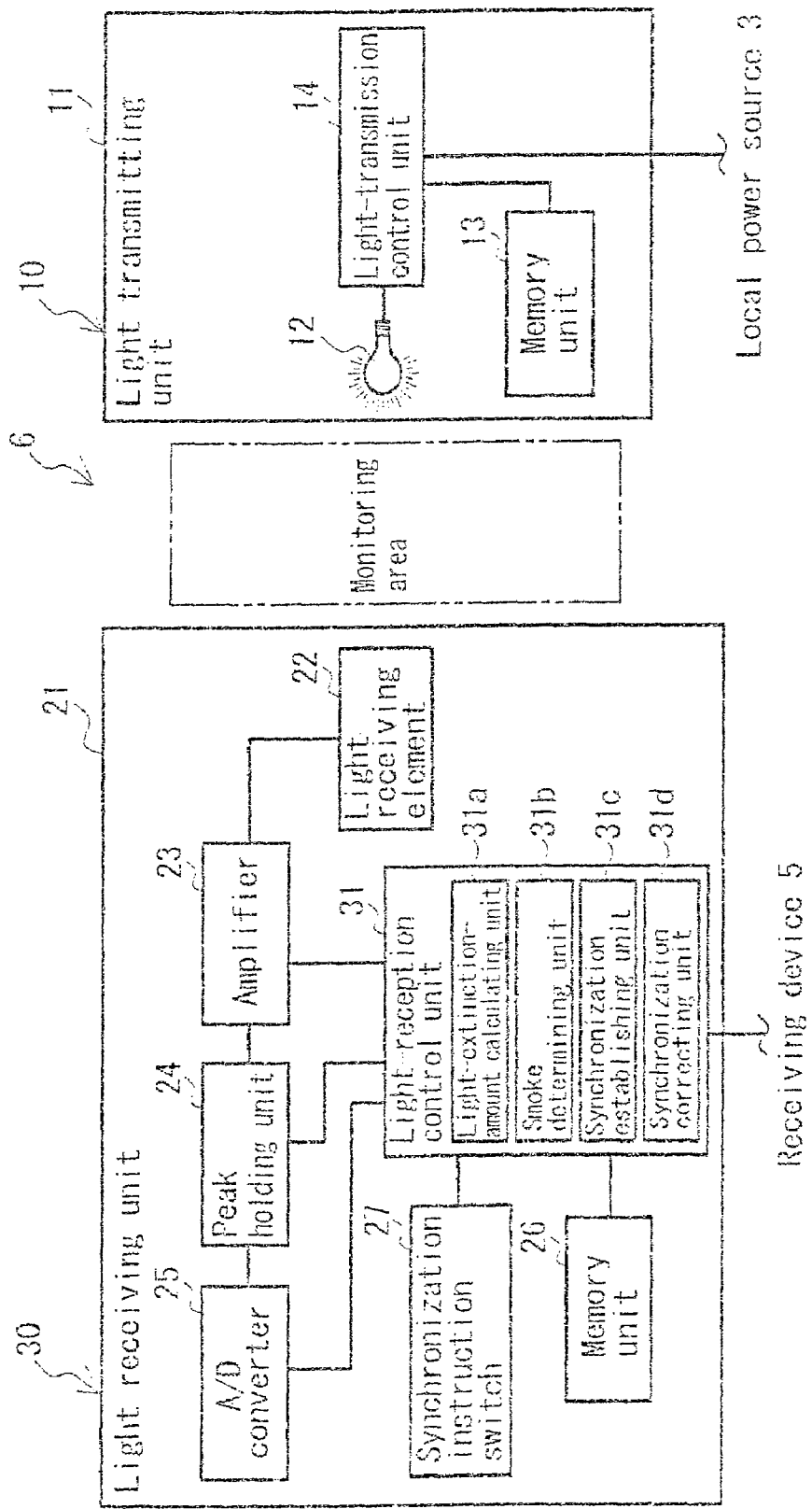
FIG. 16 is a block diagram conceptually showing main electric configurations of a light transmitting unit and a light receiving unit of a sensor according to a second embodiment.

FIG. 16 is a block diagram conceptually showing main electric configurations of a light transmitting unit and a light receiving unit of a sensor according to the second embodiment. The sensor 6 includes the light transmitting unit 10 and a light receiving unit 30. The light receiving unit 30 receives detection light, and corresponds to a light receiving unit in the claims. The light receiving unit 30 includes the light receiving element 22, the amplifier 23, the peak holding unit 24, the A/D converter 25, the memory unit 26, the synchronization instruction switch 27, and a light-reception control unit 31, within the casing 21. The light-reception control unit 31 function-conceptually includes a light-extinction-amount calculating unit 31a, a smoke determining unit 31b, a synchronization establishing unit 31c, and a synchronization correcting unit 31d. The light-extinction-amount calculating unit 31a, the smoke determining unit 31b, and the synchronization correcting unit 31d are configured similarly to the light-extinction-amount calculating unit 28a, the smoke determining unit 28b, and the synchronization correcting unit 28d, respectively. The synchronization establishing unit 31c performs a predetermined process to establish synchronization based on the detection light received by the light receiving element 22, and corresponds to a synchronization establishment process unit in the claims.

Figure 17:
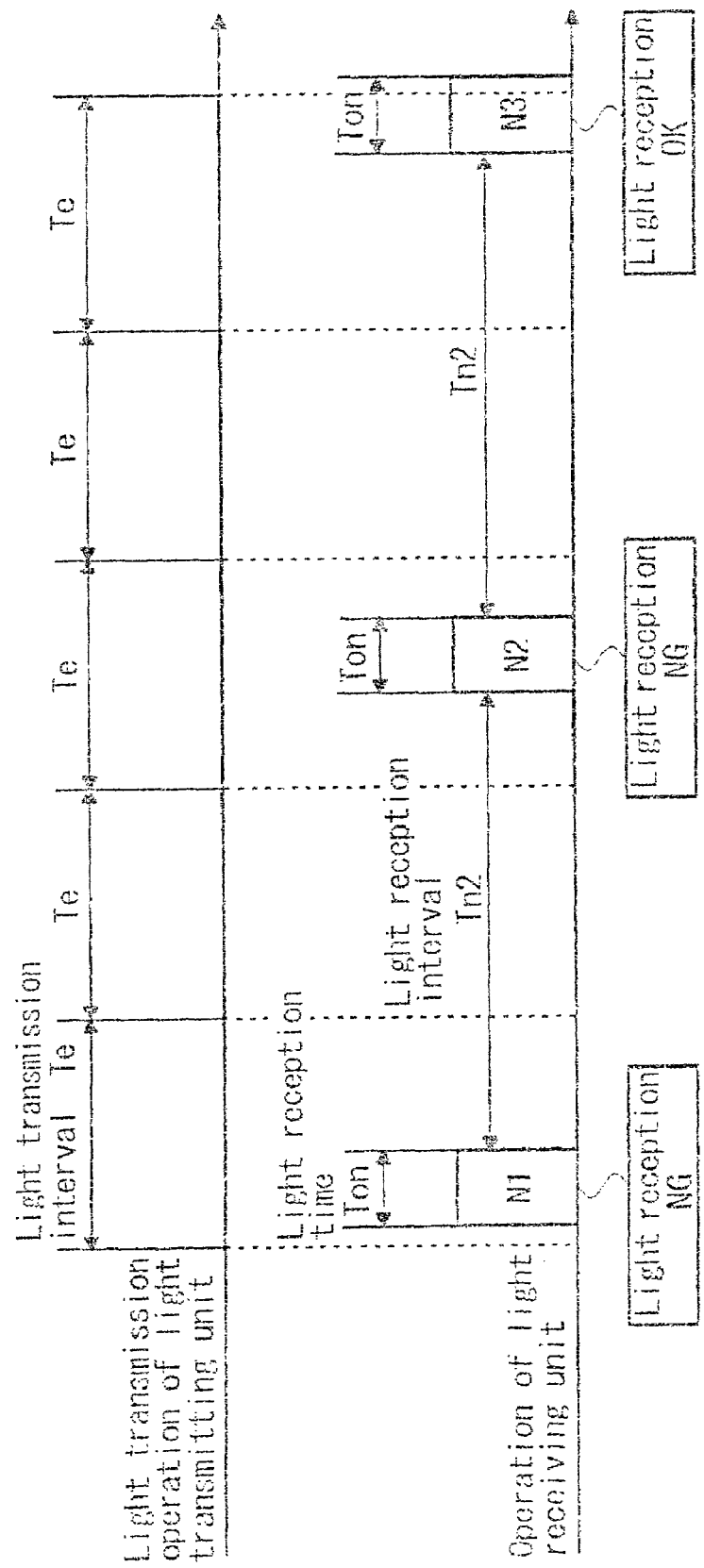
FIG. 17 is a timing chart showing the timing of a light transmission operation performed by the light transmitting unit and a light reception operation performed by the light receiving unit in a synchronization-timing specifying process.
Figure 18:
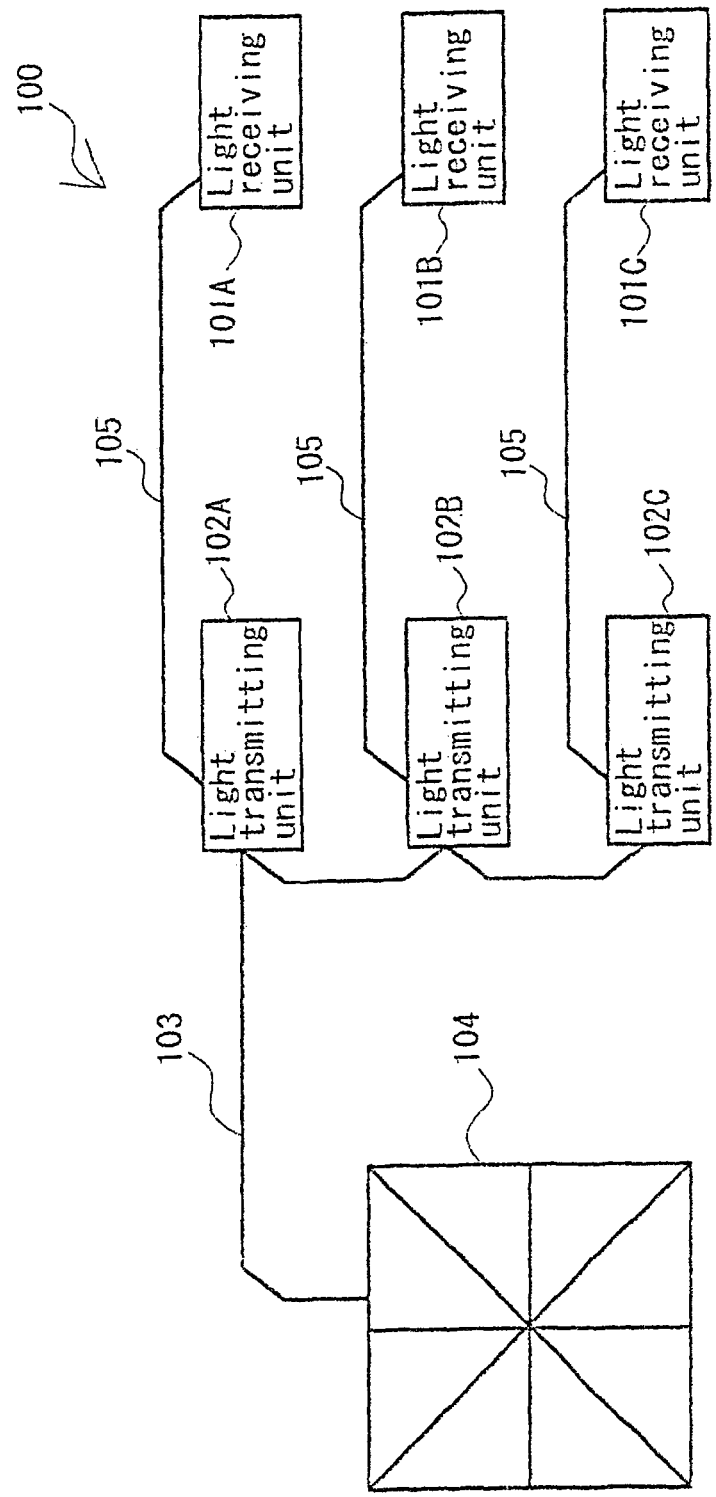
FIG. 18 is a system configuration diagram of a conventional photoelectric separated smoke sensor.

The synchronization establishment process performed by the synchronization establishing unit 31c is basically similar to the synchronization establishment process in the first embodiment, but is different in that the synchronization establishing unit 31c intermittently performs the synchronization-timing specifying process at a predetermined light reception interval longer than the light transmission interval. FIG. 17 is a timing chart showing the timing of the light transmission operation performed by the light transmitting unit 10 and the light reception operation performed by the light receiving unit 30 in the synchronization-timing specifying process. The synchronization establishing unit 31c performs the light reception operation at each predetermined light reception interval Tn2 different from the light transmission interval Te. The light reception interval Tn2 is an interval longer than the light transmission interval Te (light reception interval Tn2>light transmission interval Te). When the light transmission interval is 3 seconds, for example, the light reception operation is performed at the interval of 5 to 10 seconds. FIG. 17 shows light reception operations at three times from N1 to N3. Even when the light reception interval is set longer than the light transmission interval, the light transmission timing and the light reception timing coincide with each other at the timing corresponding to a common multiple of the light transmission interval and the light reception interval. Therefore, like in the first embodiment, the light receiving unit 30 can receive the detection light, and can specify the reference of the synchronization timing. That is, the light transmission time and the light reception time can be at least mutually different. Thereafter, synchronization can be established by performing the light-reception-time adjustment process like in the first embodiment using the synchronization timing specified in this way.

As explained above, according to the second embodiment, even when the light reception interval is set longer than the light transmission interval, the light transmitting unit 10 and the light receiving unit 30 can be synchronized, thereby obtaining effects similar to those of the first embodiment.

While respective embodiments of the present invention have been described above, the specific configurations and methods of the present invention can be modified and improved arbitrarily within the technical scope of respective inventions described in the claims. Such a modified example is explained below.

Further, problems to be solved by the present invention and effects of the invention are not limited to the above contents. The present invention can also solve problems not described above or can also have effects not described above, or can solve only a part of the described problems or can have only a part of the described effects. For example, even when the installation of the control line in the light transmitting unit cannot be completely omitted for some reason, the object of the present invention is achieved as far as the possibility of omitting the control line is increased by establishing synchronization by wireless.

The present invention includes all sensors having constituent elements performing synchronization by wireless, and can include a sensor having the light transmitting unit and the light receiving unit connected together by wire. For example, a sensor including the above-described wireless synchronization function by light, and the sensor having the light transmitting unit and the light receiving unit connected together by wire using the control line, and redundantly performing the synchronization establishment using an electric signal via this control line, and a sensor capable of omitting a local power source by supplying power to the light transmitting unit via this control line all correspond to the sensor of the present invention. For example, when a redundant configuration of the wireless synchronization and the wire synchronization is employed, it can be arranged such that the wireless synchronization is performed only when the wired synchronization cannot be established.

The configuration shown in the respective embodiments can be combined with each other. For example, both the synchronization method in the first embodiment and the synchronization method in the second embodiment can be set achievable, and any one of the methods can be selected according to the state.

While an example of using the detection light as synchronization light has been shown in the respective embodiments, a light source that transmits the light exclusive for synchronization and the light-transmission control unit 14, and the light receiving element 22 that receives the exclusive light and the light-reception control unit can be provided. In this case, the light source exclusive for synchronization and the light-transmission control unit 14 can be provided in the light receiving unit, and the light receiving element 22 that receives the exclusive light and the light-reception control unit can be provided in the light transmitting unit. Also in this case, the light transmission interval and the light reception interval can be set without receiving a limit to the light transmission interval of the detection light. Therefore, flexibility of the light transmission interval and the light reception interval improves.

In the respective embodiments, the light reception time set until the synchronization establishment is reset to the second light-reception time after the synchronization establishment. However, when it is not so necessary to perform energy saving, the relatively long light-reception time can be continuously used after the synchronization establishment. When quick performing of the synchronization establishment is not so necessary, only the relatively short second light-reception time can be used since before establishing the synchronization.

In the respective embodiments, it is explained that the synchronization correction process is performed when a predetermined synchronization-correction interval has passed. As the timing for starting the synchronization correction process, other timing can be also employed. For example, when the reception amount of the detection light decreases, there is a possibility of the occurrence of smoke, accumulation of dusts on the light axis of the detection light, and stains in the optical element such as a lens. There is also other possibility that the light receiving unit cannot receive the total amount of the detection light due to slight deviation of synchronization. Therefore, when the reception amount of the detection light decreases by a predetermined amount or more, the synchronization correction process is performed first. Thereafter, only when the reception amount of the detection light still decreases, it can be determined that smoke occurs, and the accident-warning audible signal can be output or the compensation process can be performed. Alternatively, the synchronization correction process can be started based on a predetermined control signal from the receiving device.

In addition, circuit examples, structure examples, parameters, and various numerical values shown in the above specification and the drawings are only exemplary, and can be optionally changed unless otherwise specified. For example, a part of the circuit configuration can be replaced with a program, and the whole or a part of the process content of the functions of the light-transmission control unit 14 and the light-reception control unit 28 can be achieved by hardware.

INDUSTRIAL APPLICABILITY

As described above, the separated sensor according to the present invention can be used to synchronize the light transmitting unit and the light receiving unit that are laid out separately, and is useful to promptly establish the synchronization while saving energy.

The invention claimed is:
1. A separated smoke sensor comprising:
a light transmitting unit configured to wirelessly transmit detection light to a monitoring area; and
a light receiving unit configured to wirelessly receive detection light transmitted by the light transmitting unit to the monitoring area, determine presence of smoke in the monitoring area based on a detection amount of the received detection light, and output an accident-warning signal to a receiving device that is connected to the light receiving unit via a line when the light receiving unit determines that smoke is present;
wherein the light transmitting unit and the light receiving unit are laid out separately from each other and facing each other, sandwiching the monitoring area;
wherein the light transmitting unit is configured to receive electric power from a local power source connected to the light transmitting unit or from a battery incorporated within the light transmitting unit;
wherein the light receiving unit is configured to receive electric power from the receiving device:
wherein the light transmitting unit having a light source and a light-transmission control unit;
wherein the light source is configured to wirelessly transmit the detection light;
wherein the light-transmission control unit is configured to control transmission of the detection light by the light source by a predetermined transmission time at a predetermined light transmission interval;
wherein the light receiving unit includes:
a light receiving element configured to wirelessly receive the detection light transmitted by the light source and output a voltage or a current corresponding to an amount of the received detection light;
a synchronization-establishment processing unit configured to:
 execute a predetermined process establishing synchronization between the light transmitting unit and the light receiving unit based on the detection light received by the light receiving element;
 execute a predetermined light reception operation that receives the detection light by a predetermined reception time at a predetermined light reception interval different from the light transmission interval;
 determine presence of reception of the detection light during the light reception operation, and when reception is determined; and
 specify, as a synchronization timing, a timing that arrives at a same interval as the predetermined light transmission interval, based on a timing at which the detection light is received;
a light-extinction-amount calculation unit configured to calculate a light extinction amount of the detection light received by the light receiving element based on a volt- age or current output by the light receiving element at the synchronization timing established by the synchronization-establishment processing unit; and a smoke determining unit that determines the presence of smoke in the monitoring area based on the light extinction amount calculated by the light-extinction-amount calculation unit and a predetermined threshold value.

2. The separated smoke sensor according to claim 1, wherein the light reception interval is set shorter than the light transmission interval.

3. The separated smoke sensor according to claim 1, wherein the light reception interval is set longer than the light transmission interval.

4. The separated smoke sensor according to claim 1, wherein the synchronization-establishment processing unit changes the reception time of the detection light to a predetermined second light-reception time shorter than the light reception time, after specifying the synchronization timing.

5. The separated smoke sensor according to claim 1, wherein the light receiving unit includes an amplifier configured to amplify the voltage or current output of the light receiving element, and the synchronization-establishment processing unit starts the amplifier, and after passing a predetermined time when the output from the amplifier is stabilized, determines presence of a reception of the detection light based on the output from the amplifier.

6. The separated smoke sensor according to claim 1, wherein the light receiving unit includes an amplifier configured to amplify a voltage or current output of the light receiving element, and the synchronization-establishment processing unit for determining presence of a reception of the detection light by setting the amplifier to a maximum amplification rate, and after establishing the synchronization, resets the amplifier to a predetermined amplification rate smaller than the maximum amplification rate.

7. The separated smoke sensor according to claim 1, comprising a synchronization-correction processing unit that performs a predetermined process of correcting the synchronization timing based on the detection light received by the light receiving element, after the synchronization-establishment processing unit establishes synchronization.

8. The separated smoke sensor according to claim 7, wherein the synchronization-correction processing unit compares the reception amount of the detection light received by the light receiving element with a predetermined value, thereby determining whether the detection light of a reception amount of a predetermined value or larger is received, and when the number of times when the synchronization light of a reception amount of the predetermined value or larger is not received becomes a predetermined number of times or larger, the synchronization-correction processing unit starts the synchronization establishment process by the synchronization-establishment processing unit or performs a predetermined process of notifying the occurrence of a correction trouble.

9. The separated smoke sensor according to claim 1, further comprising:

a casing for mounting the light receiving unit, the casing having a casing cover;

wherein the light receiving unit includes an instruction unit and a memory unit;

wherein the instruction unit is configured to receive an instruction for starting the predetermined process to establish the synchronization when the casing cover is closed;

wherein the memory unit configured to store a synchronization establishment flag for determining whether or not synchronization is established; and wherein the synchronization-establishment processing unit is configured to execute the predetermined process when the synchronization establishment flag is not stored in the memory unit.

* * * * *